United States Patent
Johansen

(10) Patent No.: US 8,462,344 B2
(45) Date of Patent: Jun. 11, 2013

(54) SPR APPARATUS AND METHOD

(76) Inventor: Knut Johansen, Linkoping (SE)

(*) Notice: Subject to any disclaimer, the term of this patent is extended or adjusted under 35 U.S.C. 154(b) by 331 days.

(21) Appl. No.: 12/809,242

(22) PCT Filed: Dec. 22, 2008

(86) PCT No.: PCT/SE2008/051547
§ 371 (c)(1),
(2), (4) Date: Jun. 18, 2010

(87) PCT Pub. No.: WO2009/082353
PCT Pub. Date: Jul. 2, 2009

(65) Prior Publication Data
US 2010/0271632 A1 Oct. 28, 2010

(51) Int. Cl.
G01N 21/55 (2006.01)

(52) U.S. Cl.
USPC .......................................... 356/445

(58) Field of Classification Search
None
See application file for complete search history.

(56) References Cited

U.S. PATENT DOCUMENTS
2003/0048452 A1   3/2003   Johansen

FOREIGN PATENT DOCUMENTS
EP    1593955        11/2005
JP    2002071556     3/2002

Primary Examiner — Gregory J Toatley
Assistant Examiner — Amanda Merlino
(74) Attorney, Agent, or Firm — Bacon & Thomas, PLLC

(57) ABSTRACT

An apparatus with a radiation source 100 which has means for irradiation 610 of electromagnetic radiation with a plurality of wavelengths onto a sensor surface 210 which can support a surface plasmon, and said radiation is reflected onto at least one photosensitive detector 300, and create reflectance values, characterized by that said wavelengths at said detector are separated by wavelength, forming a wavelength ensemble, in such way that a continuous response signal can be calculated using at least three of said wavelength reflectance values, finding the wavelength closest to the resonance condition and use of adjacent wavelengths to calculate said continuous response signal 510 being a function of an effective refractive index at said sensor surface 210, where, if the resonance wavelength is the first or last of said wavelengths, at least two adjacent wavelengths closest to said closest wavelength to said resonance condition are used to calculate said continuous response signal. The present invention also relates to a method.

21 Claims, 18 Drawing Sheets

SPR APPARATUS AND METHOD

FIELD OF THE INVENTION

The present invention relates to an SPR apparatus and method.

BACKGROUND OF THE INVENTION

Surface plasmon resonance, SPR, is a sensitive technique to measure optical properties at and close to a surface. SPR setups are used to follow interactions between biomolecules in real time. These interactions are characterized by rate constants such as association and dissociation constants. Moreover, equilibrium constants are measured, as characterization of epitopes of molecules of interest. The analysis involves many different molecules, such as proteins, hormones, DNA, RNA, glycoproteins, receptors, ligands etc. When a molecule binds to the immobilized target, the effective refractive index will increase at the binding spot. This change in refractive index can be detected by use of SPR, where either the resonance angle or the resonance wavelength will change. The SPR condition is given by:

$$k_{SP} = \frac{2\pi}{\lambda} \sqrt{\frac{\varepsilon_m \cdot \varepsilon_a}{\varepsilon_m + \varepsilon_a}} \quad (1)$$

Where, $k_{SP}$ is the propagation constant for the surface plasmon, $\lambda$ is the wavelength, $\varepsilon_m$ is the complex dielectric function, and $\varepsilon_a$ is the dielectric function for the ambient media, e.g. biomolecules and liquid. $\varepsilon_a$ is equal to an effective refractive index: $N_a = \sqrt{\varepsilon_a} \cdot N_a$ is measured in RIU (refractive index units), which is unitless. For practical reasons small relative RIUs are often measured in mRIU and µRIUs. The resonance condition is fulfilled when the propagation constant of the incident light parallel to the sensor surface matches $k_{SP}$:

$$\frac{2\pi}{\lambda} n_p \cdot \sin\theta = \frac{2\pi}{\lambda} \sqrt{\frac{\varepsilon_m \cdot \varepsilon_a}{\varepsilon_m + \varepsilon_a}} \quad (2)$$

i.e.

$$\sin\theta = \frac{1}{n_p} \sqrt{\frac{\varepsilon_m \cdot \varepsilon_a}{\varepsilon_m + \varepsilon_a}} \quad (3)$$

Where $\theta$ is the incident angle, and $n_p$ is the refractive index of the prism. At the resonance condition, the incident light will be absorbed in the metal film and for that certain wavelength and incident angle the reflected light will be reduced or vanish completely. The dark band that appear is denoted SPR-dip. The width of the dip depends on the wavelength and the metal used. The wavelength for which the resonance occurs is denoted the resonance wavelength.

So far the most common method to follow the interaction is to measure the resonance angle for a fixed wavelength. The resonance angle can be determined by either angular scanning or by projection of the whole angular interval of interest onto a linear detector, using a fan shaped beam. By using a two dimensional detector a line of detection spots can be used. Another method is to use wavelength scanning where the incident angle is held fixed and the wavelengths of interest are varied. The method depends on the wavelength dependence of the surface plasmon supporting metal. Also for this method a line of spots can be detected, using a two-dimensional detector.

There is a demand for detecting many spots, or a detection of a 2-dimensional area, which means that a two-dimensional sensor surface is preferred. This was first described by Yeatman in 1987, and in 1988 by Knoll et al. Because they only had two-dimensional detectors, they measured the intensity changes at the slope of the SPR-resonance dip. Measurement of only the slope of the dip has many drawbacks: limited dynamic range, low sensitivity, sensitivity to offset changes, sensitivity to dip broadening, to mention a few. The dynamic range is limited due to the fact that the SPR dip is sharp and contrast changes can only be detected at the slopes of the SPR-dip. Because an offset change e.g. from a drift at the detector or light source can't be discriminated from a contrast change an offset change will be interpreted as a change of the resonance condition, which is obviously false. The sensitivity will only be high at a small range due to the SPR dip's shape.

Johansen, U.S. Pat. No. 6,862,094, has proposed an apparatus that uses multiple wavelengths to increase the dynamic range and increase sensitivity, precision, accuracy, and throughput. There are several labs and institutions that nowadays use white light in SPR imaging. Wong et al., Tribology International 41 (2008) 356-366, and PhD thesis "Imaging surface plasmon resonance (SPR) photonic sensors", August 2007, The city Univerity of Hong Kong, uses SPR imaging with white light and use the traditional HSV-model (Hue-Saturation-Value), proposed by Smith, Computer Graphics 1978, 12(3) 12-19, to quantify the position of the SPR-dip. The HSV-method is a cyclic transformation, i.e. it represents a "color whel" with complementary colors. Wong et al. uses the SPR-dip position to make a calibration curve between SPR-position and refractive index. The method has several limitations, because the use of an ordinary camera, a wide spectral RGB-scheme is used, which gives poor sensitivity and is limited to a closed transformation in the visible spectra, and hence a reduced wavelength regime. Because one channel is blue, silver is used which has its plasma frequency above the blue regime, but has very poor chemical properties regarding stability.

By using multi-wavelength SPR imaging, several monochromatic images from the different wavelengths are combined to a pseudo color image, U.S. Pat. No. 6,862,094, Johansen in 2000. The notation color/hue could in this context be any wavelength, wavelength band, hue, or color from below UV (ultraviolet) to above IR and FIR (infrared and far infrared). The pseudo color image is preferably a 2-dimensional image, but can be a line or spot, based on a transformation from two or more monochromatic images, based on the reflectance values from each spot on the monochromatic images, where each spot on the color image has a single value: effective wavelength, dominant wavelength, color, hue or any other arbitrary value that is related to the effective refractive index on the corresponding spot on the sensor surface.

SUMMARY OF THE INVENTION

According to an aspect, the present invention is based on calculation of effective refractive indices from reflectance values using surface plasmon resonance measurement, especially imaging, but also spot and line configurations.

According to an aspect, the present invention uses an arithmetic unit, either a separate unit, such as a processor or computer, or an embedded unit within the detector(s). The arithmetic unit reads a vector of reflectance values from the different wavelength values for each spot and calculates a color/hue value for the spot. The color/hue value is typically normalized to give an effective reflective index. The normalization procedure is favorably performed by a calibration scheme. To obtain favorable properties such as a large dynamic range, high precision and accuracy, and throughput, an apparatus with special wavelength properties are proposed. An apparatus with three or more wavelength bands, with center wavelengths spaced so that the maximum slopes of the SPR-dip are used effectively in the calculation of a color/hue value. Moreover, only wavelength bands that contribute to the signal is preferably used, other are 100% eliminated, increasing signal to noise ratio. Moreover, the separation of wavelength bands is chosen so the slope (dI/dn) of the SPR-dips (in refractive index interrogation) of adjacent wavelength bands has a slopes that are close, where I is the optical intensity at the detector, and n is the effective refractive index within the probe depth, defined by the evanescent field.

There are many different versions of functions that work with the transformation to a color/hue value, such as polynomials, centroids, weighted centroids, and wavelength to color/hue transformations.

The use of many wavelengths and the powerful transformation to a color/hue value for each spot has several advantages such as, noise rejection, offset rejection, better linearity, and larger dynamic range. The proposed apparatus with proposed algorithms gives continuous and smooth calibration curves, showing a very high sensitivity over the whole dynamic range. There are several embodiments such as many or few wavelengths, different incident angles, different refractive indices of the prism, each embodiment having advantages and limitations. Dynamic range is in this context the interval for which the measurable, e.g. effective refractive index, surface concentration, layer thickness, etc, can be determined with high or acceptable accuracy and/or precision. The term high sensitivity is used as a common nomenclature to describe high accuracy, high precision, and low detection limit, which are dependent on the system's intrinsic sensitivity (slope of the calibration curve) and, errors and noise. The term color/hue, should not to be intermixed with the HSV-system proposed by Smith.

BRIEF DESCRIPTION OF THE DRAWINGS

FIG. 17: Time series of output signal for a biochemical reaction, a) a large dynamic range, b) a close up of FIG. 17a.

DETAILED DESCRIPTION OF THE INVENTION

Figure 1:
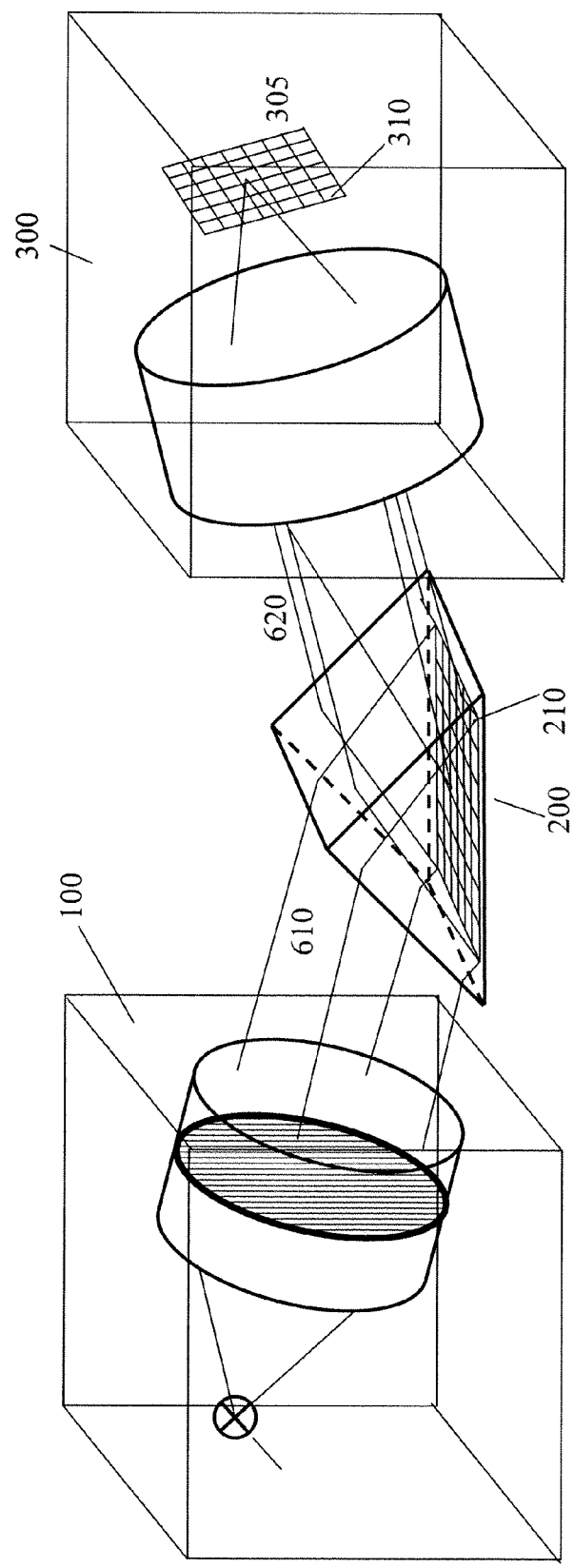
FIG. 1: SPR-imaging setup.

Now embodiments of the present invention will be described. According to an embodiment, the present invention is an apparatus and method to determine effective refractive indices (or related quantities e.g. the dielectric function, surface concentration or bulk concentration, etc) at a sensor surface utilizing SPR. The invention is especially useful for two-dimensional sensor surfaces, FIG. 1, due to the use of few wavelengths, and hence no angular or wavelength scan is necessary. Besides, leading to a simple and cost effective setup, it also leads to, high throughput, high sensitivity and large dynamic range. The invention uses preferably an arithmetic unit to calculate a number 710 or 510 which correlates to the effective refractive index at or close to the sensor surface. The sensor can support a surface plasmon, which is a surface wave propagating along a boundary between a conducting material and a dielectric. The dielectric is typical a surface with biomolecules which is surrounded by a liquid or gas, or even a solid. The resonance condition for the surface plasmon is dependent of the optical properties of the dielectricum as well as the conductive layer. Because the surface plasmon is a surface wave, it has evanescent fields associated with it. The probe depth into the dielectricum is typical a couple of hundred nanometers for visible light and gold as the metal. This means that an effective refractive index will be considered by the surface plasmon, a refractive index that can be inhomogeneous in the direction out from the surface, and along the surface. A property of a surface wave is that it has an extension along the surface. For a surface plasmon the characteristic decay length along the surface is in the order of micrometers for visible light. Gold is a common metal used as a conductive layer. The reason is that gold is free electron like, which leads to low damping of the surface plasmon, and primary, gold has good chemical stability. For biosensing, the gold layer is often covered with a linker layer, onto which capturing molecules are attached and immobilized. When free molecules bind to the immobilized molecules on the sensor surface the optical properties seen by the surface plasmon will change, i.e. the surface plasmon resonance condition change.

Figure 2:
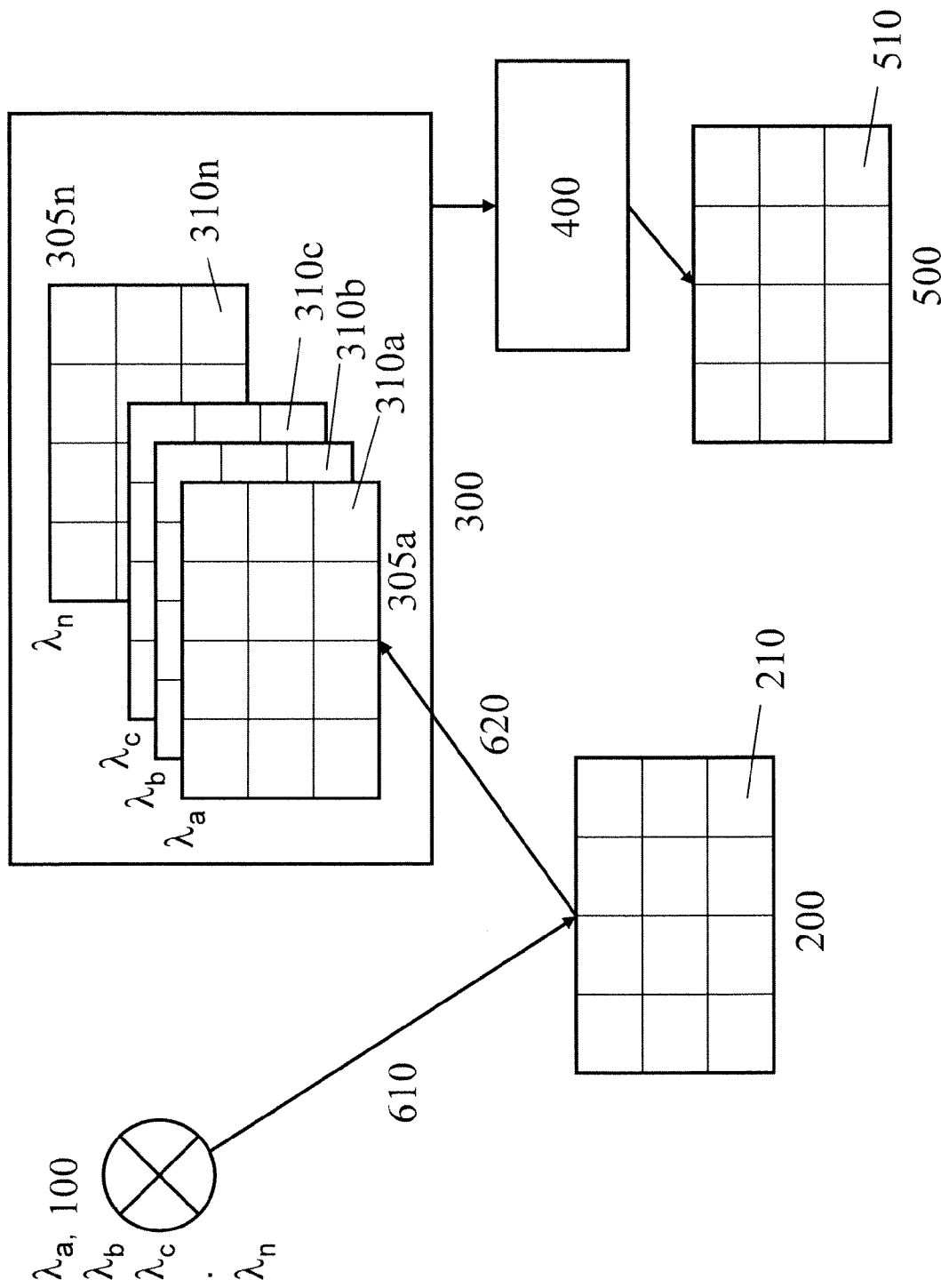
FIG. 2: SPR-imaging signal transduction.
Figure 3:
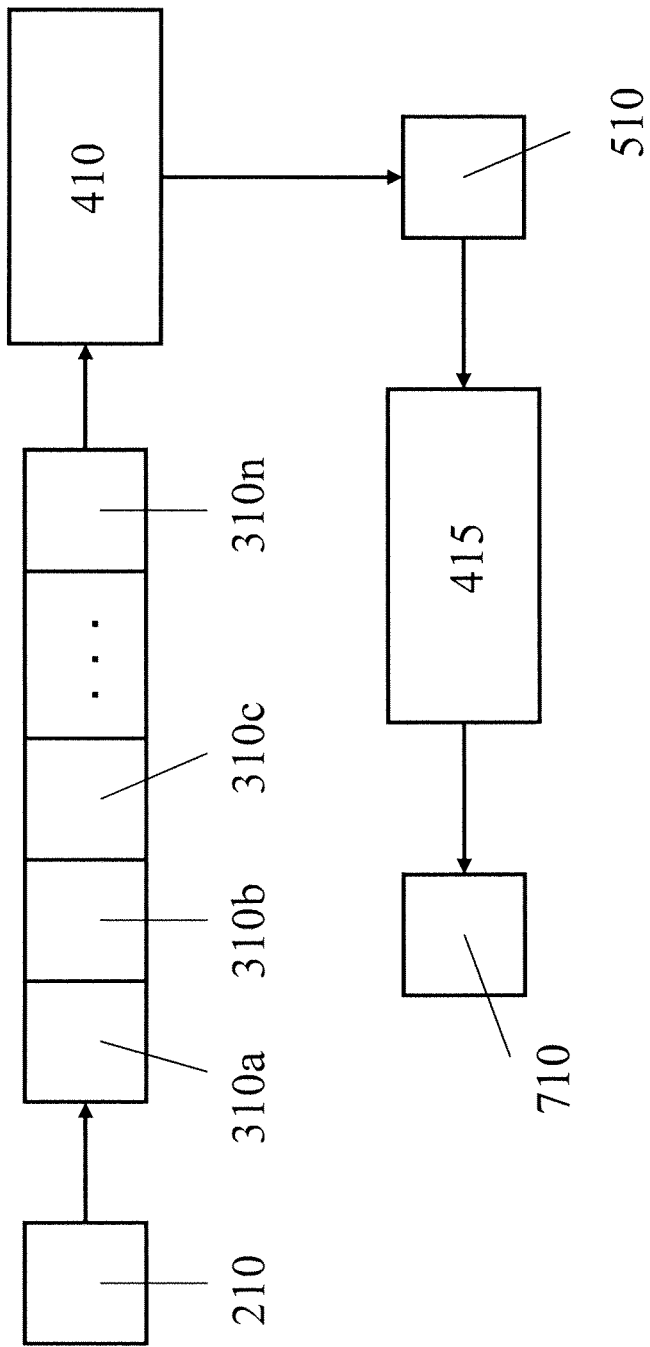
FIG. 3: Signal chain.
Figure 4:
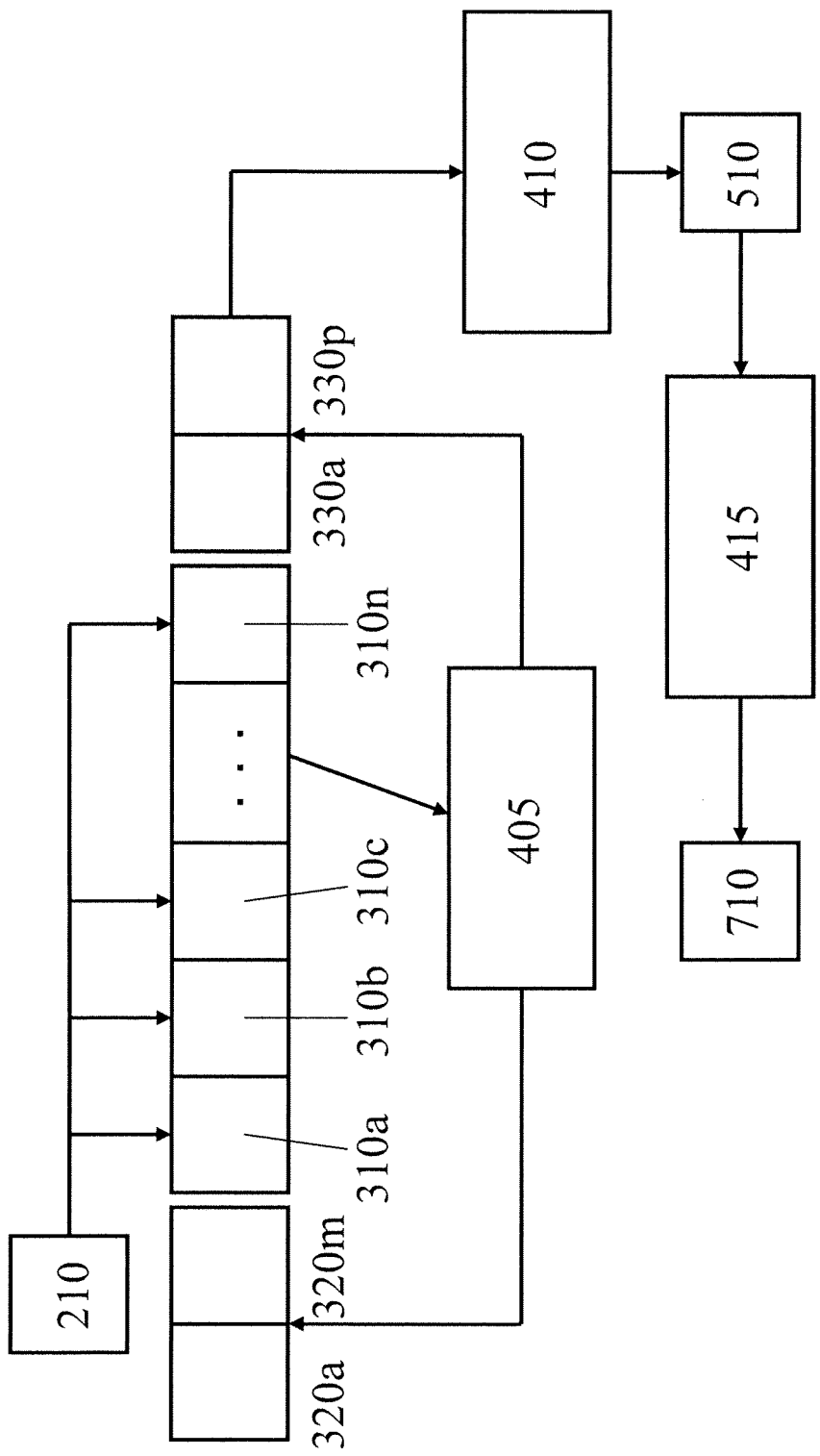
FIG. 4: Extension of wavelength vector.

In FIG. 2 and FIG. 3 is an embodiment with a 2-dimensional sensor surface shown, but the invention is not limited to this configuration, but also line and spot sensors can be used. By using a plurality of wavelengths a vector of intensity values 310 are created for each sensor spot 210 as shown in FIGS. 2 and 3. The vector is then transformed to a single value 510, which is a function of the effective refractive index at the sensor spot 210. The sensor area can be a very tiny spot or a small area which is projected onto the photo detector(s). If an area is projected, an averaging of the effective indices will automatically be performed. This averaging can have positive features such as noise reduction and more stable responses due to inhomogeneous binding of biomolecules. The vector of intensities for different wavelengths for a specific spot, can be extended mathematically, which for some embodiments are useful, e.g. some algorithms may be used that will extend the dynamic range (effective wavelength, color/hue, or effective refractive index at the sensor spot), as shown in FIG. 4. The vector can be extended in both ends 320 and 330, as shown in FIG. 4. Useful algorithm is linear or second order extrapolation, which is preferably performed by a processor 405.

By the notation wavelength, is meant a wavelength band, symmetric or asymmetric, typically 10 nm to 50 nm, but is not limited to these values.

Light Source

Figure 14:
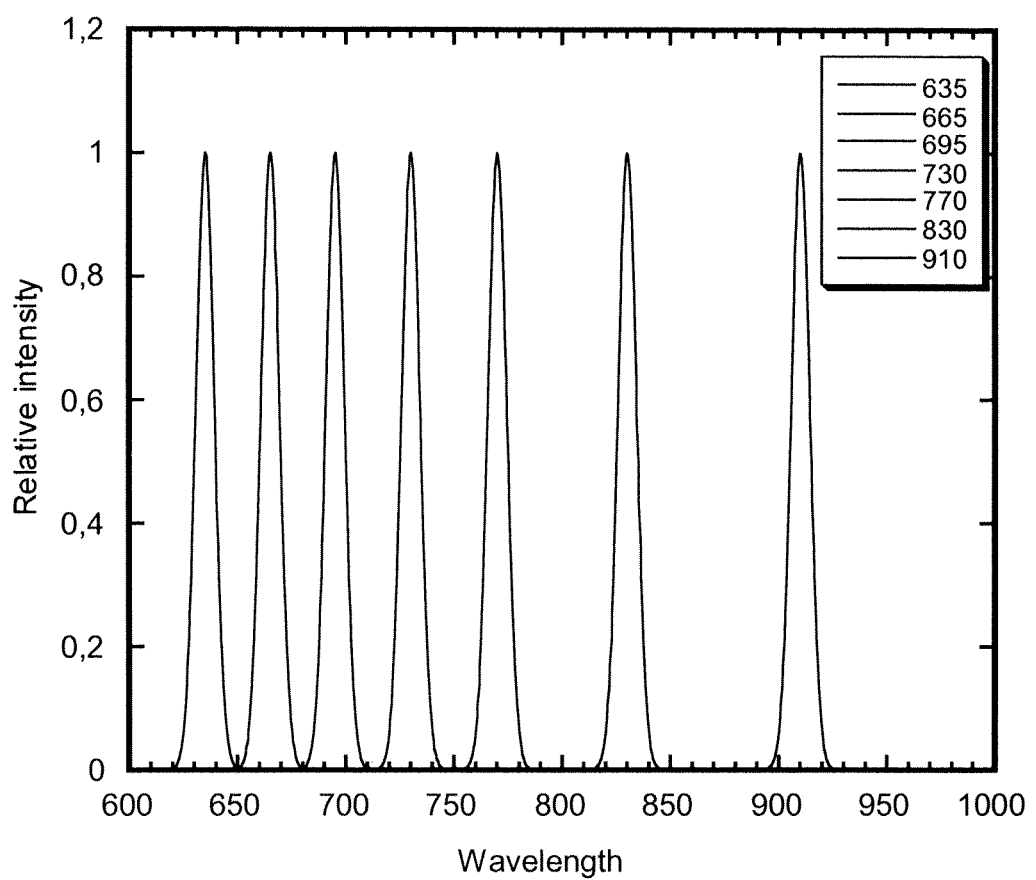
FIG. 14: Typical wavelength spectra used.

The light source 100 which irradiate the detector consist of discrete wavelength bands or dominating wavelengths band. FIG. 14 shows a spectra, or wavelength ensemble, with dominating wavelengths of 635, 665, 695, 730, 770, 830, and 910 nm, each having a 10 nm full width half maximum (FWHM) of 10 nm. A narrow wavelength band will give a narrow SPR-dip which is characterized by step flanks and deep resonance minima. A suitable FWHM is 1 to 50 nm, and more preferable 5 to 25 nm. A too narrow band will lead to a reduced optical power (which can lead to higher noise) but not much sharper dip. A broad wavelength band will lead to less steep flanks at the SPR dip and lower instrument sensitivity and hence higher noise. Hence an "optimal" FWHM can be chosen, which is dependent on the optical setup used. The most preferably wavelength band is in the 10 nm regime, but the invention is not limited to this. There is an advantage to irradiate the sensor with discrete wavelengths, instead of illuminating the sensor with broadband wavelength interval, such as "white light" and then after the sensor surface discriminate different wavelengths, in such way that for a broad wavelength interval, the sensor surface will be heated by light that is not used for measurement. With "white light" is meant a more or less continuous spectra with a large wavelength interval, not necessary in the visible region.

A discrete wavelength source can be designed with a "white light source" such as a Tungsten Halogen lamp, an arc lamp such as a Xenon lamp, or equivalent, with a set of filters, e.g. rotating interference filters. A discrete wavelength source can also be made of discrete wavelength devices such as light emitting diodes (LEDs) or LASERs, without or in conjunction with filters.

The use of separated discrete wavelengths means that the "resonance minimum" is not directly tracked, but the flanks of the dip are used to track the movement of the resonance. Because the SPR-dip is well defined, this is a more effective method to follow the resonance condition, using the most sensitive part of the SPR-dip. Due to a quota of differences offsets are 100% rejected, and other drifts, and dip changes are also effectively rejected.

Figure 5:
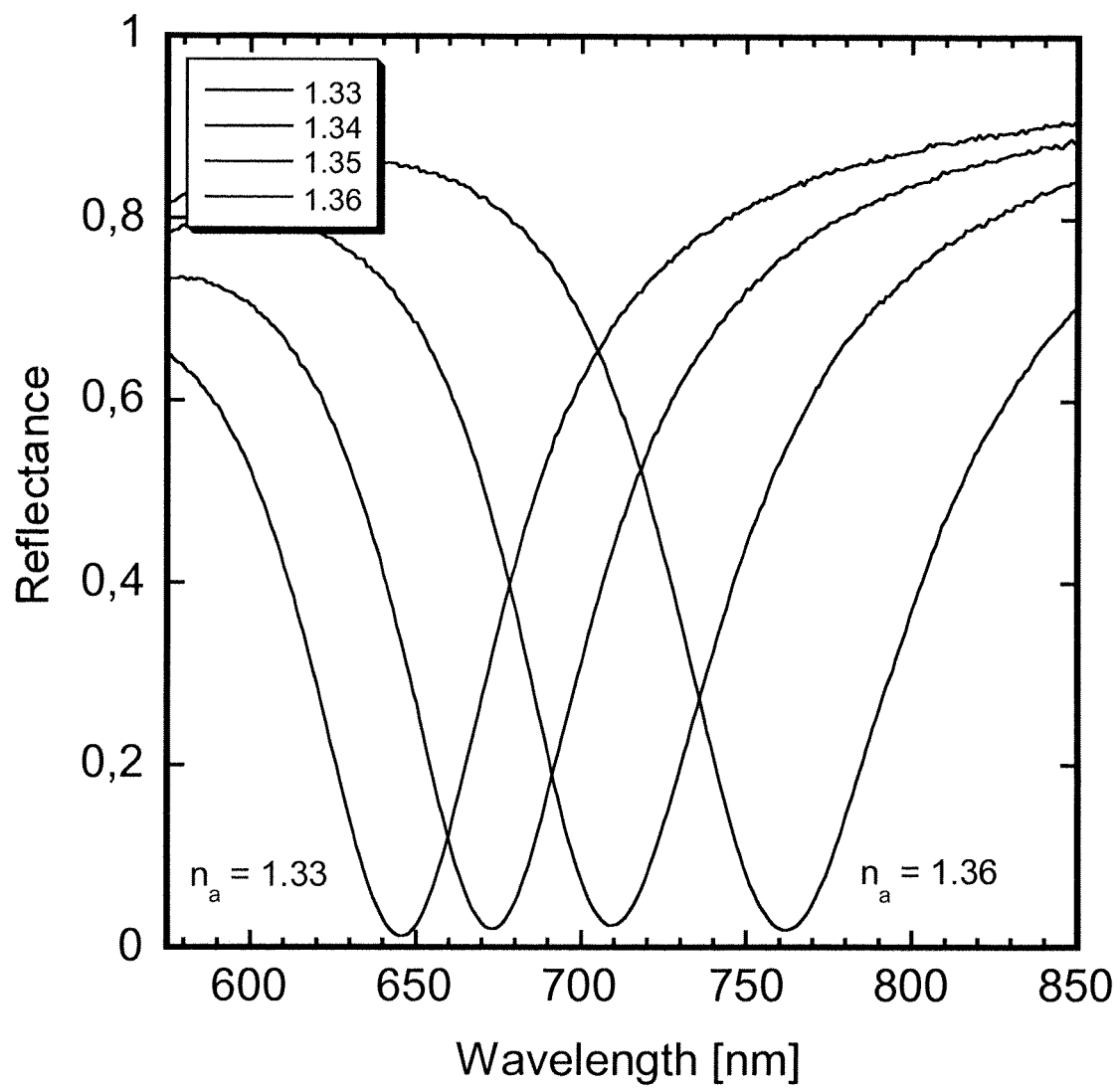
FIG. 5: Reflectance vs. wavelength.
Figure 15:
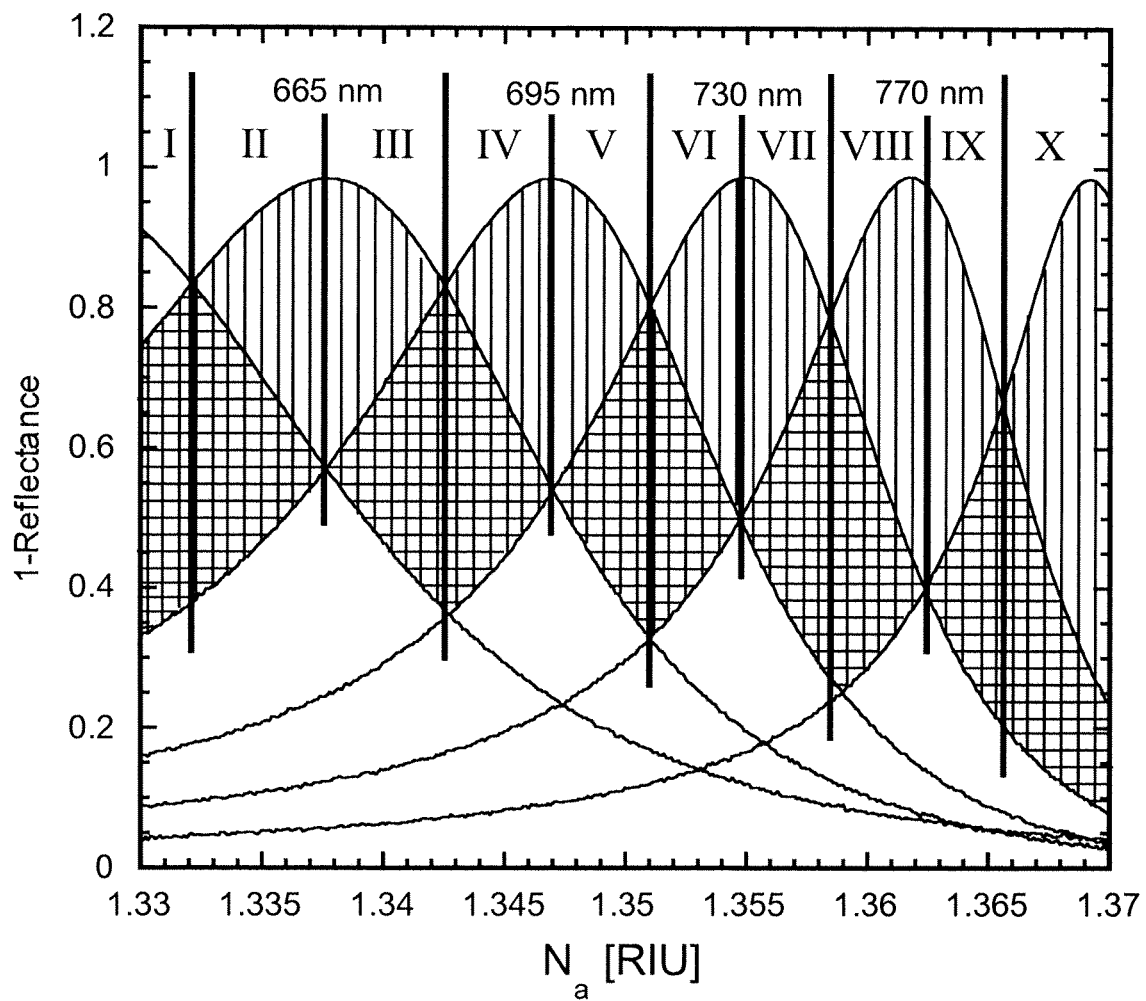
FIG. 15: Detector signal from wavelength spectra.
Figure 16:
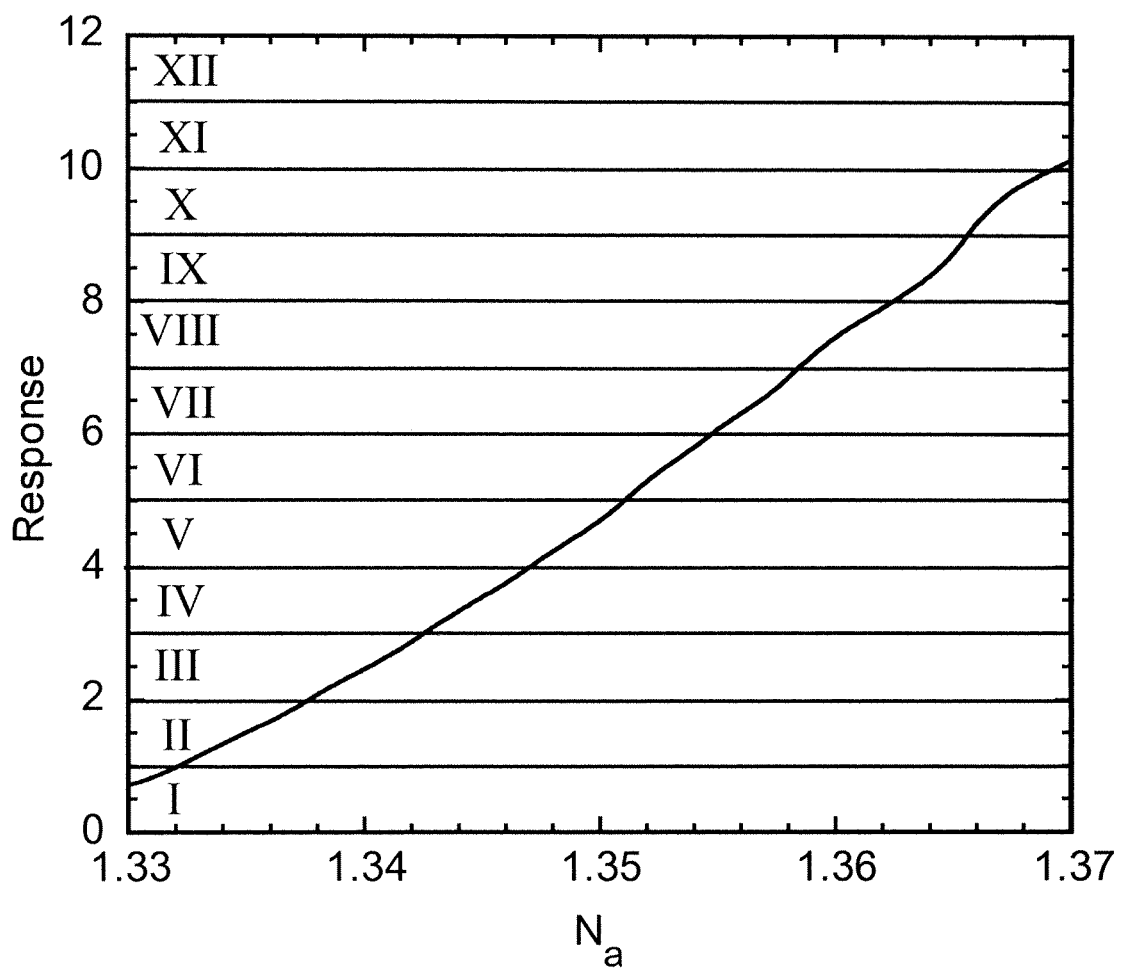
FIG. 16: Response signal (Oligo-Lamda) from a 7 segment spectra.
Figure 18:
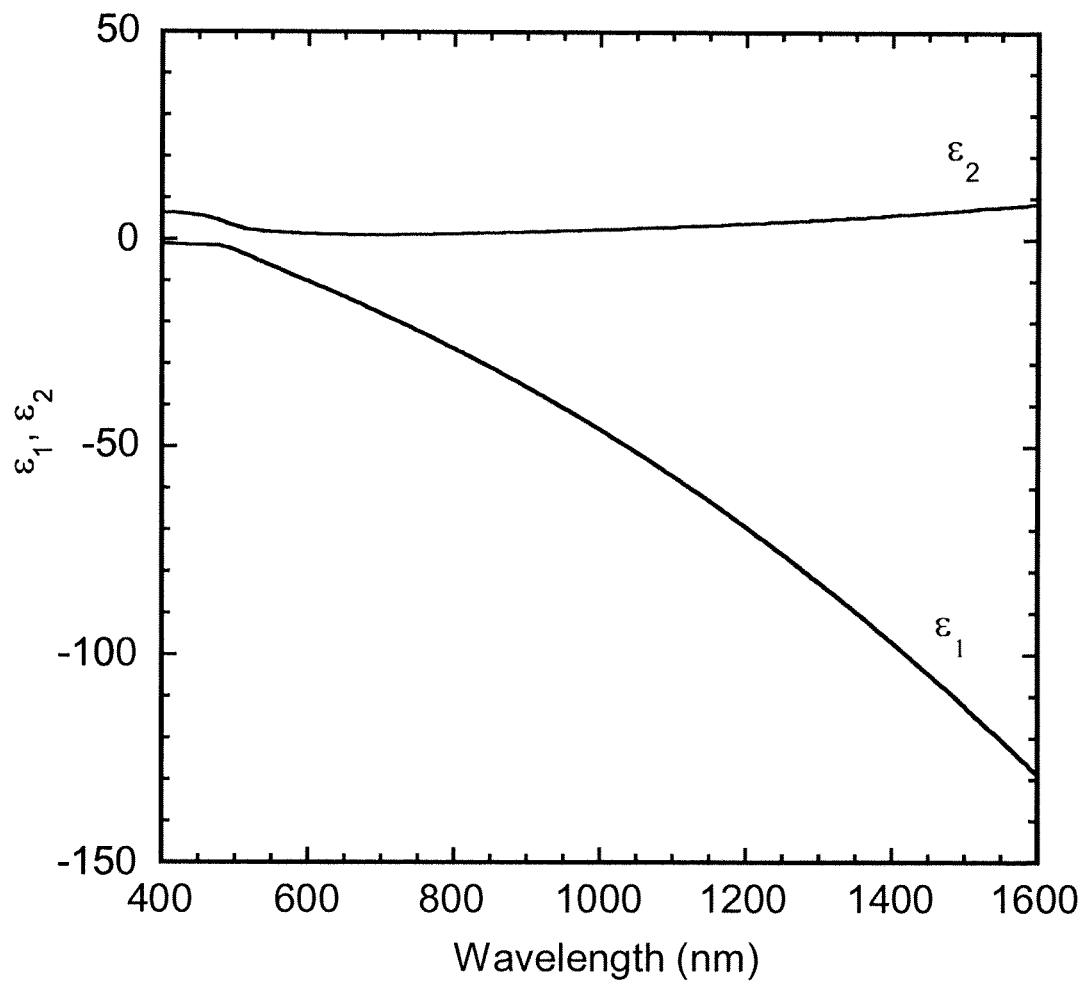
FIG. 18: Dispersion relation for gold.

The choice of spectra used is dependent on the application and complexity of the instrument. The wavelengths used are dependent on the incident angle, the refractive index of the prism, the SPR supporting metal, and the effective refractive index at the sensor surface. The relations between these parameters are given by the dispersion relation in equations 1 to 3. The refractive index of the prism define the incident angle, and a high refractive material such as SF11 glass (n=1.8) will lead to smaller incident angles than an ordinary crown glass such as BK7 (n=1.5). Smaller incident angle will lead to less distortion (compression of a two-dimensional image in one direction). The major mechanism for the sensor is the dispersion relation for the SPR-supporting material. Gold is stable and free-electron like, which makes it suitable as a SPR-supporting material. The dispersion relation, e.g. the dielectric function E, versus wavelength is shown in FIG. 18 (data from Johansen et al. Rev. of Sci. Instr., 2000, 71(9), 3530-3538). A wavelength interrogation of SPR is shown in FIG. 5, for gold and BK7 prism, for different effective refractive indices, ranging from 1.33 to 1.36, Due to the dispersion relation of the SPR-supporting material, the spacing in e.g. nm between wavelengths have not to be equidistant. For some response methods, as shown in FIG. 14 and FIG. 15, it can be favorable to use non-equidistant wavelengths.

The number of wavelengths used is a compromise between, complexity (and cost), linearity, noise and dynamic range. The more wavelengths used, the larger dynamic range can be achieved. The larger spacing used will mostly lead to worse linearity, and often more noise. However, different response signal methods have different properties. As shown in FIGS. 6-16, the Oligo-lambda method has very good performance with few wavelengths used. Examples with three and seven wavelengths are shown.

Example

Area Detector

FIGS. 2 to 4 show the signal transduction from a multi-spectral light source 100, which illuminates 610 the sensor surface 200, where a single or plurality of sensor elements 210 or an arbitrary sensor area (area, line or spot) are positioned. The reflected light 620 hits one or a plurality of photo detectors 300, where each wavelength (or a group of wavelengths) creates an image $305a \ldots n$. On each image $305a \ldots n$ is there an associated pixel $310a \ldots n$ that corresponds to an area 210 on the sensor surface 200. The images $305a \ldots n$ are converted to one image 500 by algorithms in an arithmetic unit 400, where one spot 210 on the sensor 200 is given a single value 510, which is a function of the effective refractive index on the sensor surface. With a single value is meant that a plurality of scalars (vector) is by an arithmetic unit 410 reduced to a scalar. However, parallel calculation with different algorithms can create a plurality of values for each sensor spot. Moreover, monitoring a sensor area 210, over time will lead to a vector of output signals 510 (many frames). However, every single element are based on a plurality of wavelengths. The output signal 510 is supposed to be continuous and monotonic with regard to the effective refractive index at the sensor 200. However, the output signal is often not linear. This means that a calibration or normalization scheme is preferably followed, where the output signal 510 is converted to a calculated effective refractive index 710 by an algorithm in an arithmetic unit 415.

Example

Line or Spot Detector

The invention can be used for a single spot sensor or a line sensor. Because these configurations are subsets of an area detector, a detailed description is not necessary. However, the proposed invention simplifies the optical setup and hence a cost effective apparatus with high sensitivity and arbitrarily large dynamic range. If only one sensor spot is used, only a spot photo detector is needed. Accordingly, for a line sensor only a line photo detector is needed.

Color/Hue Algorithms

There are several algorithms (which are listed below) that can perform the transformation from a pattern of many wavelengths to an effective wavelength or hue, and many calibration schemes (listed below). The transformation is simplified and unambiguous, due to the fact that a single dip (or peak) is followed, emanation from the SPR condition.

The use of many wavelengths means that a larger range of effective refractive indices at the sensor spot can be measured than if only one wavelength was measured. There is often a need for large dynamic range. With a large dynamic range, small and large responses can be measured simultaneously, large difference in immobilization levels can be used, wide range of buffers and solutions can be used to mention a few.

With the use of several (more than 3) sharp resonance dips, e.g. emanation from more free electron metals such as silver, or long range plasmon (LRP) setups, still an arbitrarily large dynamic range is achievable. A sharper resonance dip leads inherently to a larger signal to noise ratio.

Moreover, the use of many wavelengths makes it possible to simultaneously measure at descending and ascending flank on the surface plasmon resonance dip. This means that offset drifts and dip broadening can effectively be rejected, see FIG. 11, leading to higher accuracy in measurements. There are different possibilities to calculate an effective refractive index for a spot, like color/hue calculation using a few wavelengths, e.g. two, three, four, five etc, or using centroid algorithms, which are useful when many wavelengths are used. Of course, there are embodiments where ordinary polynomial such as quadratic, third order or even higher order algorithms can be used. However, it has for angular interrogation been shown, Johansen, Measurement, Science and Technology, 2000, 11(11), 1630-1638, that centroid, and especially weighted centroid algorithms are effective, regarding linearity, signal to noise and calculation performance, and hence the same is expected for many wavelengths. For embodiments few wavelengths such as two, three, four etc, the color/hue method is very useful.

Extension of Dynamic Range

If many wavelengths are used, an extrapolation of the wavelength range can be performed. By such procedure a larger dynamic range can be obtained, without increasing the number of wavelengths. If chosen properly, the dynamic range can be extended, especially when using centroid or weighted centroid algorithms. Typical linear and second order extrapolation can be used.

Effective Wavelength or Color/Hue Calculation

Figure 6:
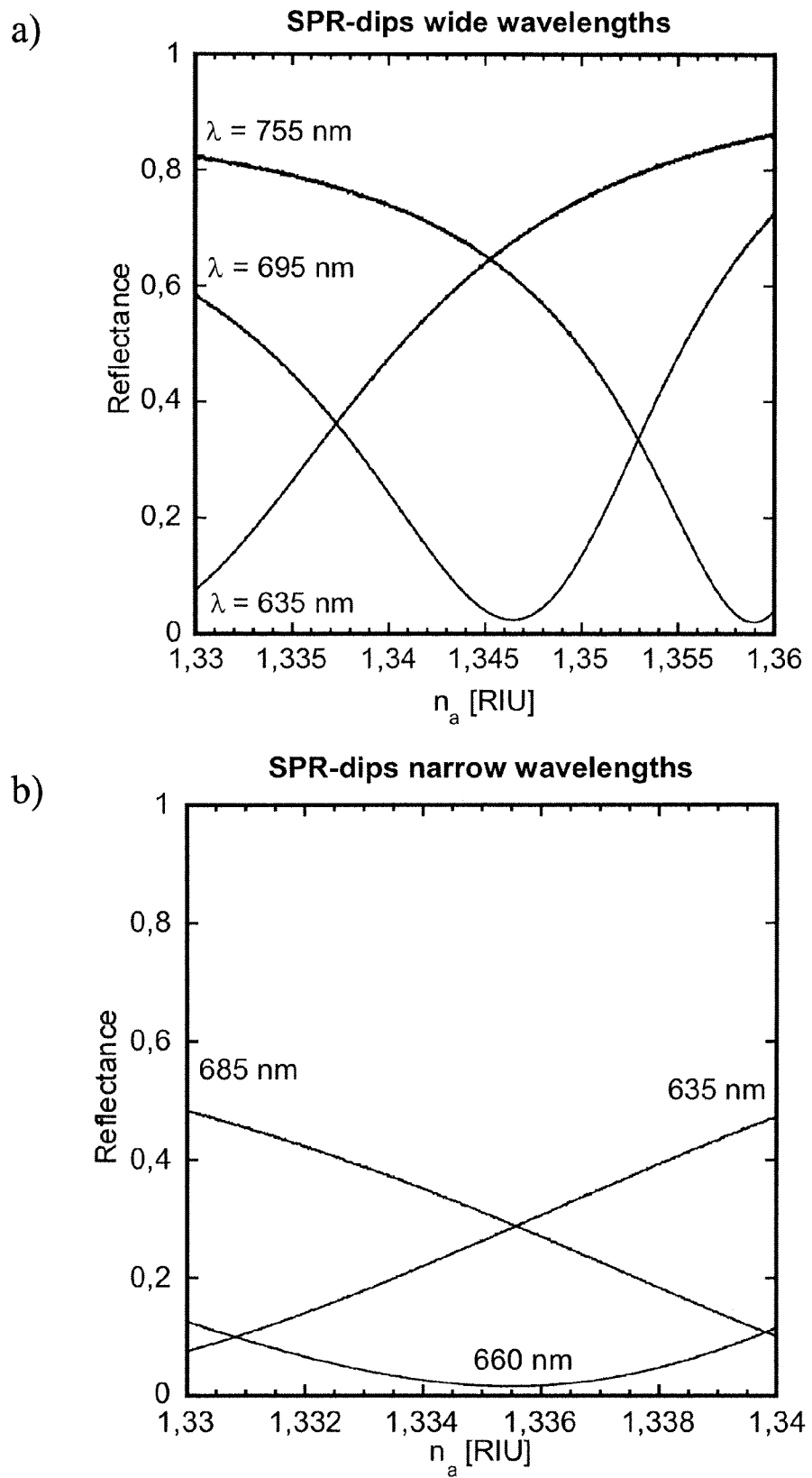
FIG. 6: Reflectance vs. refractive index, a) wide wavelengths, b) narrow wavelengths
Figure 7:
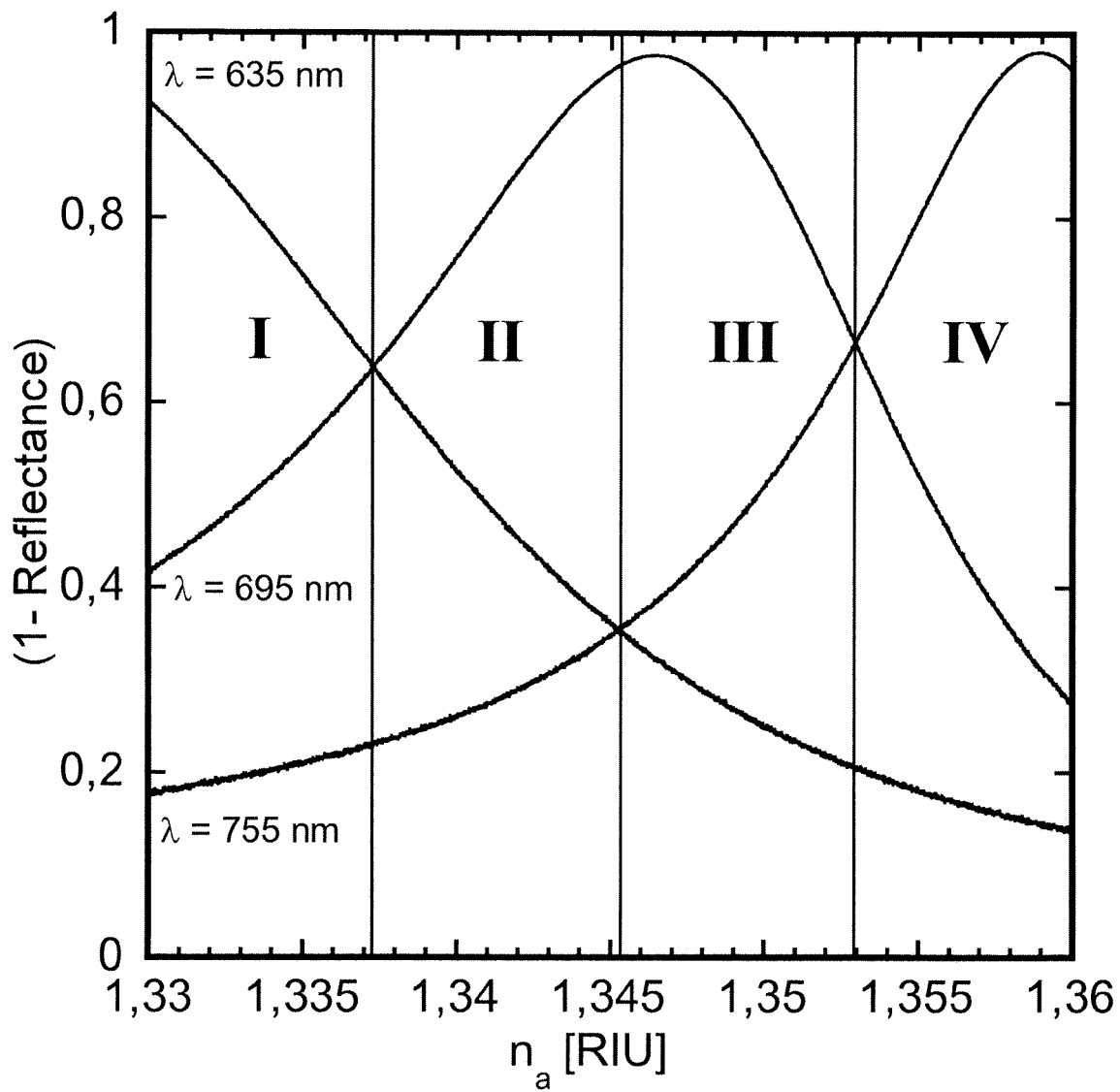
FIG. 7: (1-reflectance) vs. refractive index.

Different algorithms for calculation of are outlined:
Hue
Polynomial
Centroid
Weighted centroid Oligo-Lambda-Method A transformation scheme from a multiple wavelength scheme is proposed, that is by the inventor denoted Oligo-Lambda. If a few wavelengths are used it is possible to use differences between reflectance values divided by another difference of other reflectance values. Using three or more wavelengths, the calculated color/hue is always continuous. By comparing the relative intensities for the different wavelengths a scheme can be outlined. Inverting the SPR-dips will create peaks, absorption, which may be easier to interpret, but not change any physical or mathematical meaning.

$$A_i = 1 - R_i \quad (4)$$

Where $A_i$ is the amplitude for the peak, as shown in FIG. 7, and $R_i$ is the reflectance, as shown in FIG. 6, or signal from the detector for wavelength i respectively, and i is an index, denoting increasing wavelength. The first wavelength index is here set to be zero and the last z, where index one concern the lowest wavelength. In this example both $A_i$ and $R_i$ can have values between 0 and 1, but arbitrary values can be used, because a quote is calculated. An example, but not limiting, of a useful scheme is outlined:

Find wavelength with maximum amplitude $A_i$, denoted $A_{max}$, i.e. index i is equal max. We can denote the wavelength closest to the resonance condition $\lambda_{max}$.

There are two principal cases, 1) if $A_{max-1} > A_{max+1}$ $$\text{Color/Hue} = -(A_{max-1} - A_{max+1})/(A_{max} - A_{max+1}) + 2 \cdot \text{max} \quad (5)$$

2) if $A_{m+1} < A_{m-1}$ $$\text{Color/Hue} = (A_{max+1} - A_{max-1})/(A_{max} - A_{max-1}) + 2 \cdot \text{max} \quad (6)$$

At the ends the formula has to be explicit written as:
First segment: if i=1=max:

$$\text{Color/Hue} = (A_1 - A_2)/(A_0 - A_2) \quad (7)$$

Last segment: if i=z=max:

$$\text{Color/Hue} = -(A_{z-1} - A_{z-2})/(A_z - A_{z-2}) + 2 \cdot (z) \quad (8)$$

FIG. 15 shows a 6 wavelength system, where the bold vertical lines mark the integers of the Oligo-Lambda function (OL-function). There are 2·(z−1) segments. Thin horizontal lines, marks the numerator in the OL-function, and thin vertical lines, the denominator. A careful choice of wavelength values will minimize differences between numerators (and denominators) at segment borders, which will increase linearity. A suitable choice of wavelengths is to try to make the numerator in equation 5 to 6 and 10 to 11 the same size. This means that the reflectance value for the wavelength adjacent to the wavelength "closest to the resonance condition" ($\lambda_{max}$) has to be equal, or close to equal, as the second closest wavelength at the opposite side of the "wavelength closest to the resonance condition" ($\lambda_{max}$), or in other words: Said apparatus and method according to any of claim 1-10, where said wavelengths are chosen such as, when said effective refractive index at said sensor surface has a value such as the two wavelengths that are closest to the resonance condition have the same reflectance level, and that the adjacent wavelengths to these said two wavelengths, have the same, or close to the same level, too. It can be noticed that the numerator utilizes the steepest slope of both the SPR-dips, and therefore the "sensitivity" is twice of a traditional reflectance measurement. The denominator is almost constant, as can be seen in FIG. 15. Because the nominator is zero at one segment border, and equal to the denominator at the other border, the response signal will always have a value between zero and one. This does not hold at the end of the wavelength ensemble, but still the response signal is useful into a part of the segment. Because the numerator utilizes the most linear part of the SPR-dip, the linearity is excellent throughout the whole dynamic range, as shown in FIG. 19, where a seven wavelength system is shown.

For a three wavelength system the algorithm can look as:

$$A_2 \geq A_1 \geq A_0: \text{Color/Hue} = -(A_1 - A_0)/(A_2 - A_0) + 4\text{IV} \quad (9)$$

$$A_1 \geq A_2 \div A_0: \text{Color/Hue} = (A_2 - A_0)/(A_1 - A_0) + 2\text{III} \quad (10)$$

$$A_1 \geq A_0 \geq A_2: \text{Color/Hue} = -(A_0 - A_2)/(A_1 - A_2) + 2\text{II} \quad (11)$$

$$A_0 > A_1 \geq A_2: \text{Color/Hue} = (A_1 - A_2)/(A_0 - A_2)\text{I} \quad (12)$$

Sparse Wavelengths

FIG. 6a and FIG. 7 shows how a three wavelength system may look like with quite spread (sparse) wavelengths (635, 695, and 755 nm, i.e. by 60 nm separation) leading to a curvature in the response signal 510, as shown in FIG. 8a, and a quite large dynamic range ($N_a$=1.33 to 1.36). The noise figures can easily be investigated by looking at the residuals (actual curve minus a fitted curve), which are shown in FIG. 9a. The signal chain in FIG. 9a has an offset added to the detector signal, which is completely rejected, but would have resulted in erroneous signal if pure reflectance measurement have been used (prior art), which is shown in FIG. 9b. Because three wavelengths are used, three curves can be chosen from in FIG. 9b, and all have reduced dynamic range, offset errors and high noise.

Narrow Wavelengths

FIG. 6b shows how a three wavelength system may look like with close (narrow) wavelengths (660, 635 and 685 nm, i.e. by 25 nm separation) leading to less curvature in the response signal 510, as shown in FIG. 8b, but shows a reduced dynamic range ($N_a$=1.33 to 1.34). The noise level (FIG. 10a) is reduced compared to the sparse system (FIG. 9a), and offsets are 100% rejected. Reflectance measurements (prior art) have no offset rejection and higher noise figures, as seen in FIG. 10b. Moreover, FIG. 11a shows that the Oligo-Lambda-method effectively rejects dip broadening, e.g. due to inhomogeneous binding to the sensor surface. FIG. 11b shows residuals from reflectance measurements, which show that there is no rejection for dip broadening.

Figure 8:
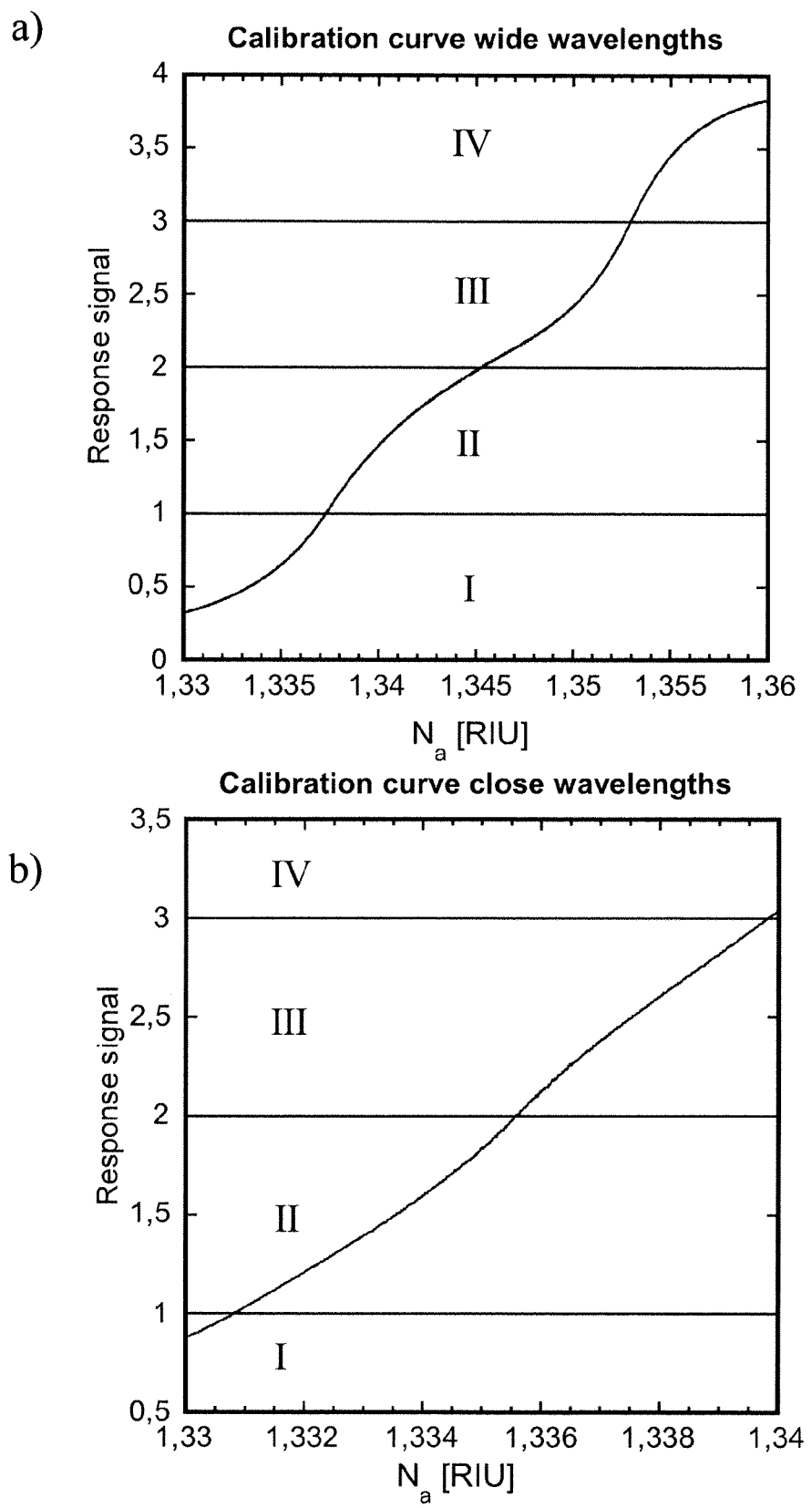
FIG. 8: Calibration curves hue, a) wide wavelengths, b) narrow wavelengths.
Figure 9:
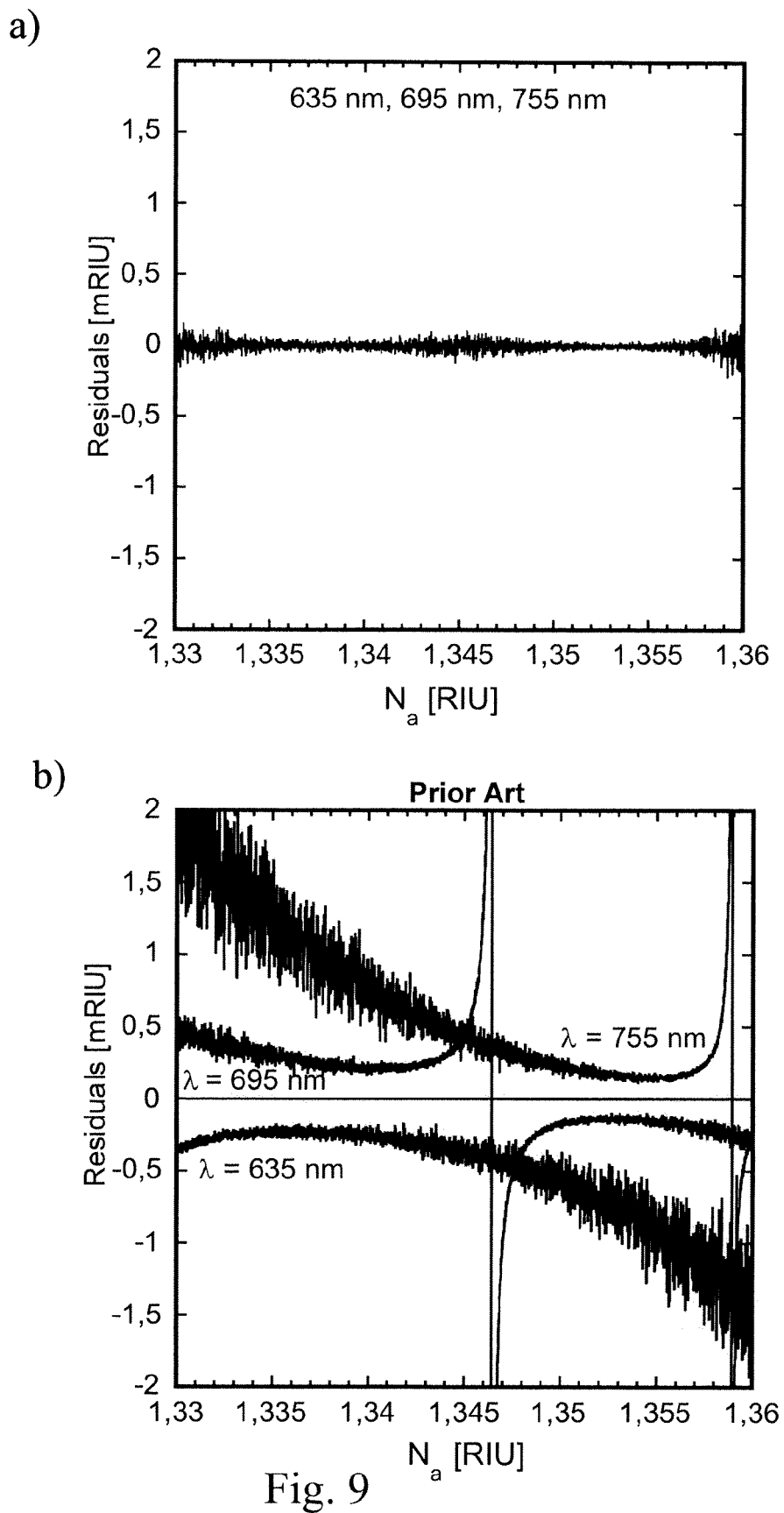
FIG. 9: Residuals, wide wavelength range, with offset and noise, a) hue-method, b) reflectance method (prior art).
Figure 10:
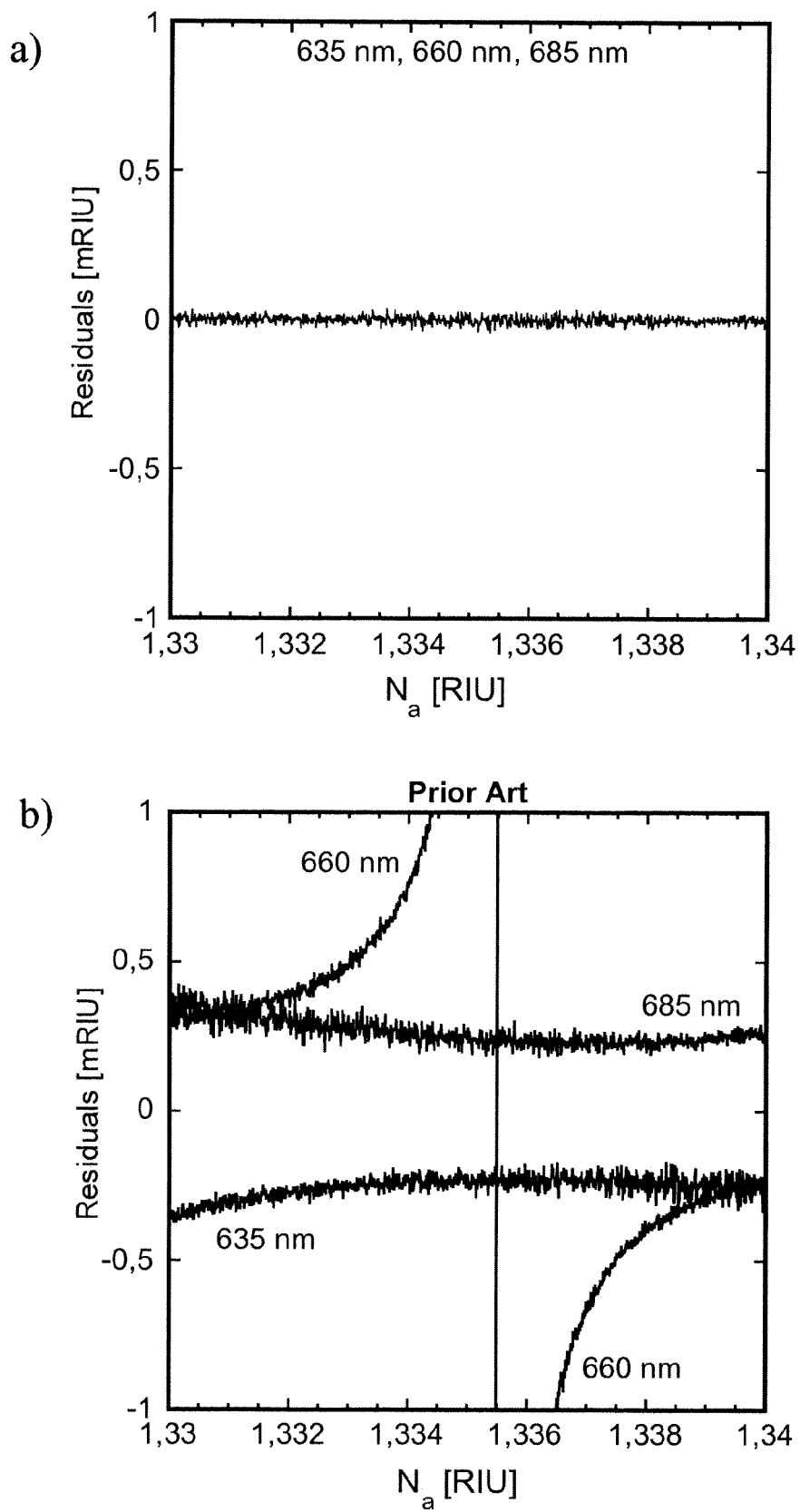
FIG. 10: Residuals, narrow wavelength range, with offset and noise, a) hue-method, b) reflectance method (prior art).
Figure 11:
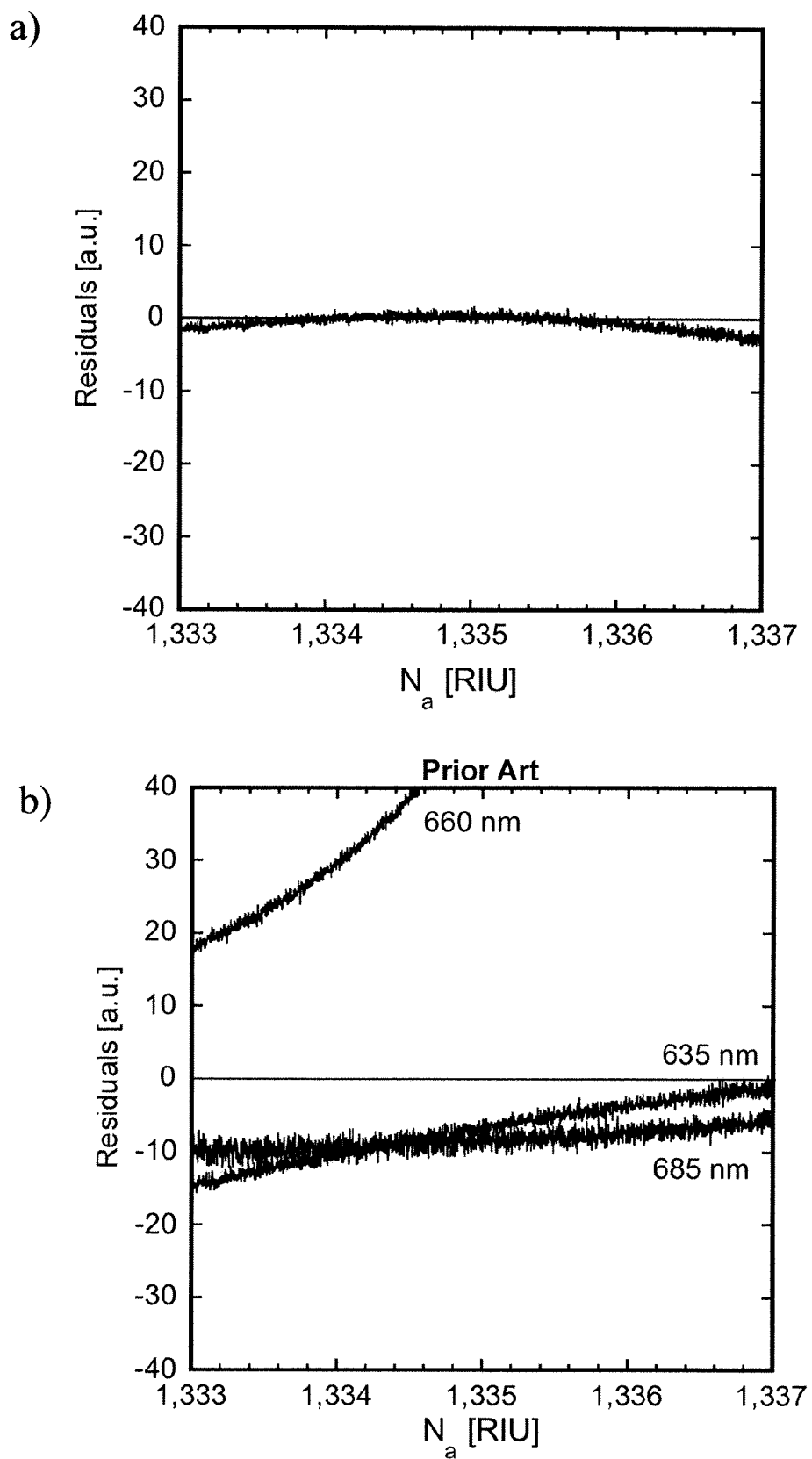
FIG. 11: Residuals, dip broadening, a) hue-method, b) reflectance method (prior art).
Figure 12:
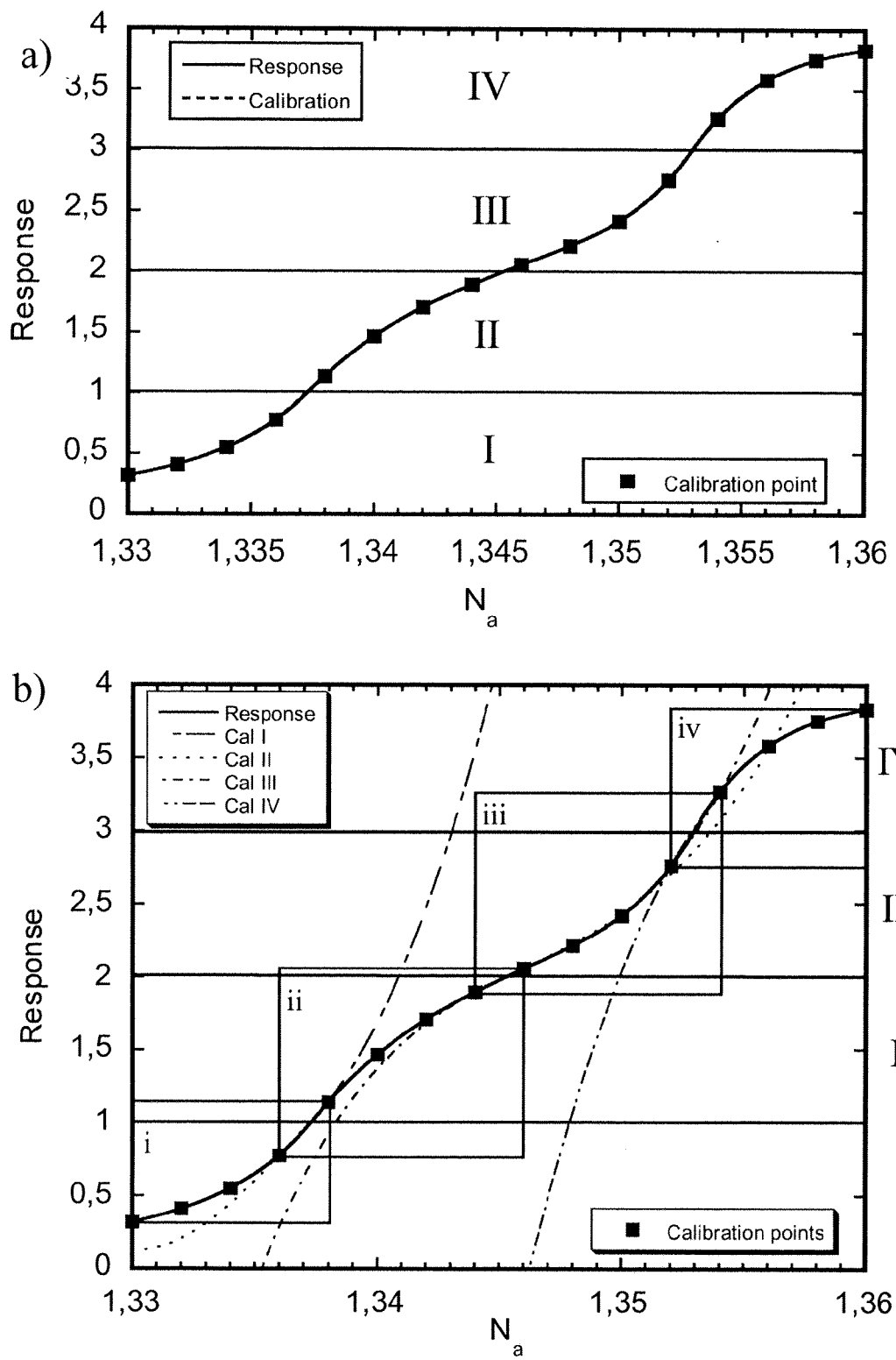
FIG. 12: Calibration curve, a) cubic spline, b) segmented cubic spline.

There are three intercept between the $R_i$ curves, and hence there are four Color/Hue segments denoted I, II, III, and IV, respectively as shown in FIG. 7. The Color/Hue values can in this case obtain values from zero to 4, as shown in FIG. 8. To obtain a $N_a$, the calculated color/hue response signal is inputs to a calibration curve. The calibration curve can be a look up table (LUT), or a mathematical function, e.g. polynomial, cubic spline etc.

The Oligo-Lambda-method can have an arbitrary wide dynamic range. This is a big difference and an advantage compared to Smiths HSV-system, which is a closed system, and hence will have a reduced dynamic range.

Calibration Curve

FIG. 3 shows the transformation from a vector 310 of reflectance values, where each element corresponds to a certain wavelength. These elements 310a-n are transformed to a response signal by e.g. the Oligo-Lambda method, e.g. in an arithmetic unit 410. In this case the response signal is a color/hue signal, which for the Oligo-Lambda method is unitless. Because, the response signal curve, is not a straight line that passes origin, but have some curvature, despite small, normalization or calibration is preferred. When a calibration is performed, the output signal 710 will have the units in RIU, or if calibrated to another arbitrary unit, that unit.

Cubic Spline

Because there are different color/hue segments, or response segments, there may be some sensitivity ($dA_i/dn$) differences at the color/hue segment borders. These are taken care of at the calibration procedure. An embodiment of a calibration procedure is outlined using cubic spline; As shown in FIG. 12a only a few (here, in the order of ten) calibration points are needed to obtain a near perfect fit. However, the fit is worst at the color/hue segment borders, due to the change of color/hue-formula, which leads to a very small change in the slope of the calibration curve. The fit will be better the tighter the calibration points are close to the color/hue segment borders. However, an embodiment is outlined which lead to near perfect fit, using a segmented overlapping cubic spline.

Overlapped Segmented Cubic Spline

Figure 13:
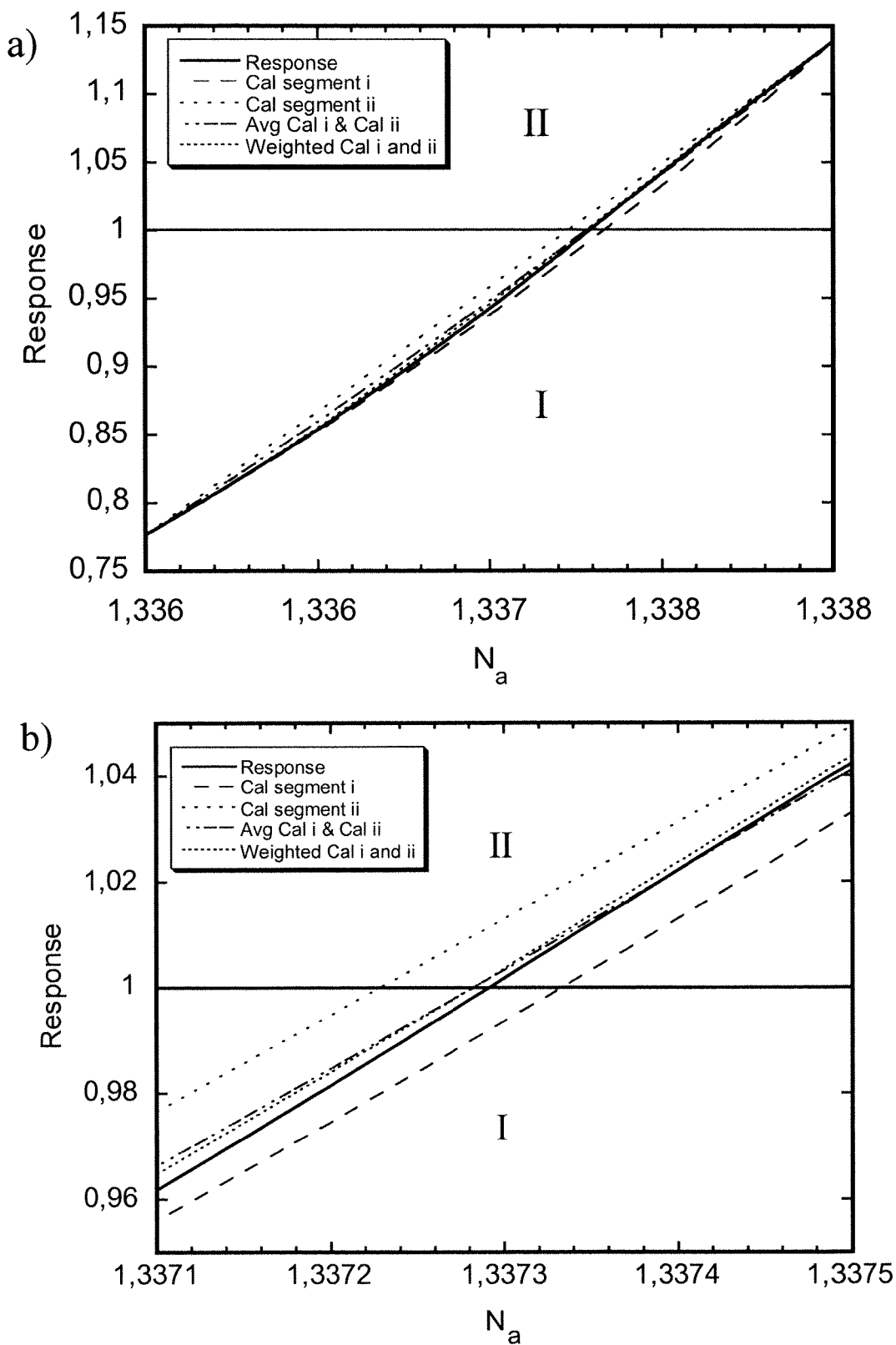
FIG. 13: Close up calibration curve, segmented cubic spline.

In an embodiment, each color/hue segment (I to IV) has a cubic spline function associated to it. In FIG. 12b the border between response segment I and II is shown. If the different spline functions for the different color/hue segments where not interconnected the calibration curve would be discontinuous, which can be unfavorable. By using the calibration point at the adjacent color/hue segment, cubic line function will overlap, as shown in FIG. 11b. At the color/hue segments borders there will be two calibration curves. Either curve can be used, but both will not have optimal accuracy. These are shown in FIGS. 13a and b as the outer curves. Moreover, it will be a little sensitivity (dose/response) change at the change of calibration segment. This can be overcome, as outlined. An embodiment uses an intermediate calibration curve, which is shown in FIG. 13 as the dada-dotdot-curve, which is created as the arithmetic mean of the two calibration curve segments at the color/hue segment border. However, this method is not optimal, leading to small kinks at the calibration points. A more preferred embodiment is proposed, where a pseudo calibration point (refractive index), Np, is placed at the color/hue segment border for the intermediate calibration curve. The color/hue segment border is easy to find because the calibration curve is an integer at the color/hue segment border. It should be noted that the real color/hue segment border (from measurements) is not exactly on the same position as the calibration color/hue segment border, but very close. An embodiment uses this point to perform a new cubic spline fit. The different calibration segments will now be continuous. Yet another most preferred embodiment uses the pseudo calibration point, but uses it to calculate a new intermediate segment which has a 50/50 weight of the two cubic spline segments over the color/hue segment border, and a linear weight to 100% to the calibration points for the two cubic spline curves respectively. This means that the intermediate curve will follow the original calibration curve close to the original calibration point. In an embodiment the calibration curve between the last calibration point at the first segment at to the color/hue segment border is:

$$C = cs1 \frac{2N_p - N_{c1} - N_a}{2(N_p - N_{c1})} + cs2\left(1 - \frac{2N_p - N_{c1} - N_a}{2(N_p - N_{c1})}\right) \quad (13)$$

Where C is the new intermediate calibration curve, $cs_1$ and $cs_2$ are the original overlapping calibration curves at the color/hue segment border, respectively. $N_{c1}$ is the last calibration point (refractive index) at the first segment, and $N_a$ is the refractive index (continuous). This calibration is very close to the true response, and is shown as the dotted line in FIG. 13. The calibration at the other side of the color/hue segment border, and other color/hue segment borders are solved similarly. Examples are graphically shown in FIG. 12 and FIG. 13.

As mentioned, the calibration color/hue segment border is not exactly the same as the measured color/hue segment border. However, the calibration color/hue band border can easily be adjusted when a measured signal reaches the real hue band border (two intensities are equal). The result is an almost perfect calibration.

The hue method has several advantages, besides being a continuous function regarding changes in effective indices, the derivative of the function $d(Color/Hue)/dN_a$ is also continuous. Moreover it is has a 100% rejection of common offsets, which means an unstable light source will not give any false signals.

Polynomial

Polynomial curve fitting can be used to obtain a dip minimum position. An embodiment uses a second order fit, assuming equidistant wavelength bands.

$$\lambda_{eff} = [0.5 + (R_1 - R_2)/(R_1 - 2R_2 + R_3)]\Delta\lambda + \lambda_{start} \quad (14)$$

Where $\lambda_{eff}$ is an effective calculated wavelength, $\Delta\lambda$ is the separation between wavelengths, and $\lambda_{start}$ is the first wavelength. $R_2$ corresponds to the smallest reflectance value, and $R_1$ and $R_2$ are the reflectance levels for the adjacent wavelengths. For four and more wavelengths, the $R_2$ value is chosen as the smallest reflectance value. $A_{eff}$ is for these cases adjusted by an integer, $n_\lambda$:

$$\lambda_{eff} = [0.5 + n + (R_1 - R_2)/(R_1 - 2R_2 + R_3)] \cdot \Delta\lambda + \lambda_{start} \quad (15)$$

The method will generate a continuous response signal (e.g. $\lambda_{eff}$ or $N_{a\_out}$, where $N_{a\_out}$ is a calibrated response signal in RIU) shift of wavelengths, because change of wavelength sets are performed when the two smallest reflectance values are the same, and hence the two corresponding sets will have the same minimum point. Because the second order function is not precisely the same function as the reflectance function of the different wavelengths, there will be an approximately periodical residual error with the period of change of wavelengths sets. However, this periodical is easily corrected by a function as well as cubic splines and look up tables. Suitable functions are second and third order functions, where zeroes of the correction function is placed when the two smallest reflectance values are equal, i.e. at wavelength set shift. An embodiment with a second order polynomial with a second order correction looks like:

$$\lambda_{eff\_corr} = \lambda_{eff} + Corr_2 \quad (16)$$

Where $$Corr_2 = 4E_2(X_{frac} - 0.5)(X_{frac} + 0.5) \quad (17)$$

and where $X_{frac}$ is the decimal part from the relative deviation from $X_{min}$, $X_{min}$ is the position in A where the lowest intensity occurs. The wavelength vector $(\lambda_1, \lambda_2, \lambda_3 \ldots \lambda_n)$ corresponds to a vector $(X_1, X_2, X_3 \ldots X_n)$, where the separation of the X elements are one, i.e. $(1, 2 \ldots n)$. $X_{frac}$ is $X_{min}$ minus $X_{rounded}$ where $X_{rounded}$ is the rounded value (i.e. $X_{rounded}$ is an integer) of $X_{min}$. Therefore $X_{frac}$ has a value between $-0.5$ and $+0.5$. $E_2$ is the amplitude of the residuals from true position and calculated position, preferably the amplitude of the residual at the position minus the amplitude at the position between two positions. Other embodiments may define $E_2$ as:
1) the amplitude of a least square fit of a second order polynomial with the roots at the middle between wavelength positions,
2) the peak to peak residual from the algorithm error, i.e. maximum of $|\lambda_{min} - \lambda_{eff}|$.

Because $Corr_2$ has zero amplitude when the two smallest wavelengths are equal, i.e. at wavelength set shifts, the corrected function is also continuous.

Another embodiment with a second order polynomial and a third order correction is exemplified:

$$\lambda_{eff\_corr\_3} = \lambda_{eff} + Corr_2 + Corr_3 \quad (18)$$

Where $$Corr_3 = -32/3 E_3 (X_{frac} - 0.5)(X_{frac} + 0.5) X_{frac} \quad (19)$$

and where $E_3$ is chosen as maximum of $|\lambda_{min} - \lambda_{eff}|$. Other embodiments may use other third order polynomials, as far as two roots are at $-0.5$ and $+0.5$. A least square fit will give the amplitude $E_3$ of the correction term.

Because the $Corr_3$ has a zero amplitude when the two smallest wavelengths are equal, i.e. at wavelengths set shifts, the corrected function is also continuous. The correction functions are based on the difference in shape between a SPR-dip and a polynomial and hence to a high degree deterministic and can therefore be set once, or at least very seldom. The Correction functions are dependent on wavelength spacing, incident angle, and the effective refractive index.

Cubic spline functions and look up tables are easily performed by calibration from known refractive indices at the sensor surface. Useful calibration solutions are sucrose and glycerol solutions. The number of calibration points is dependent on the accuracy needed. In general, the calibration has two purposes, to calibrate for non linear movement of the reflectance minimum over the detector, and normalization of algorithm errors, i.e. for the case the mathematical algorithm does not follow the SPR-dip exactly.

These are examples of different embodiments, and the invention is not limited to equidistant wavelength spacing or the other features.

Centroid

The use of centroid is particular useful if many wavelengths are used, e.g. more than five. An example of an embodiment is:

$$\lambda_{eff} = \frac{\sum_i [\lambda_i \cdot (I_i)]}{\sum_i [I_i]} \quad (20)$$

Where $\lambda_{eff}$ is an effective wavelength, $\lambda_i$ is the wavelength and $I_i$ is the intensity for index i, respectively.

To enhance signal to noise ratio a weight which is dependent on the reflectance values can be added to the centroid formula. Because there is more information at the wavelengths which have low reflectance values, than the wavelengths which has high reflectance values, the SPR-dips can be inverted mathematically as shown in equation 4. An embodiment is when the weight function is a function with zero at reflectance is one, and then increasing:

$$\lambda_{eff} = \frac{\sum_i [\lambda_i \cdot w_i(I_i)]}{\sum_i [w_i I_i]} \quad (21)$$

The weight $\omega_i$ can be an arbitrary function, but an example of an effective weight is the inverted reflectance signal itself, $A_i$. This leads to:

$$\lambda_{eff} = \frac{\sum_i [\lambda_i \cdot (A_i^2)]}{\sum_i [A_i^2]} \quad (22)$$

Moreover, signal to noise can be further enhanced by the introduction of a limiting level L. The introduction of L means that wavelengths that are close to 1 in reflectance will be omitted, which is favorable because they contain little signal and contain mostly noise. One embodiment will then look like:

$$\lambda_{eff} = \frac{\sum_i [\lambda_i \cdot w_i(A_i - L)]}{\sum_i [w_i(A_i - L)]} \quad (23)$$

If the limit is excluded or set to 1 in reflectance value the output signal will be insensitive to common offsets, i.e common offset rejection, COR, is 100%. The introduction of a L different from 1, introduces sensitivity errors as well as sensitivity to common offset errors. The sensitivity errors are to a high degree deterministic and can easily be corrected by the same methods descried for the polynomial method.

Yet another embodiment of the weighted centroid method looks like:

$$\lambda_{eff} = \frac{\sum_i [\lambda_i \cdot (A_i - L)^p]}{\sum_i [(A_i - L)^p]} \quad (24)$$

Where p is an arbitrary number. A preferred embodiment is for p=2.

Parallel Algorithms

Because all algorithms uses the same wavelength values, the different algorithms and variants can be processed in parallel or as post processing. This is particularly useful when time dependences are investigated, such as association and dissociation rates for molecules.

Advantages

The algorithms described will properly designed, outperform reflectance measurement in every aspect, such as:
 Offset rejection (100% vs 0%)
 Large dynamic range (at least tenfold)
 Low noise (at least tenfold)
 High sensitivity (at least tenfold)
 There are three major error sources:
 Short time errors (noise)
 Medium time errors (fluctuations)
 Long time errors (drifts)

Short Time Errors

Short time errors set signal to noise ratio, and hence sensitivity (e.g. detection limit). Short time errors are easy to detect but can be difficult to reduce.

Medium Time Errors

Fluctuations from light source and detector, or fast and changing drifts are difficult to detect and therefore difficult to measure and reduce.

Long Term Errors

Long term errors such as drifts, are easy to detect and compensate.

The proposed method reduces all three error sources, and especially the dangerous fluctuations are virtually eliminated. The important short time noise is tenfold reduced over the dynamic range.

Time Series

Figure 17:
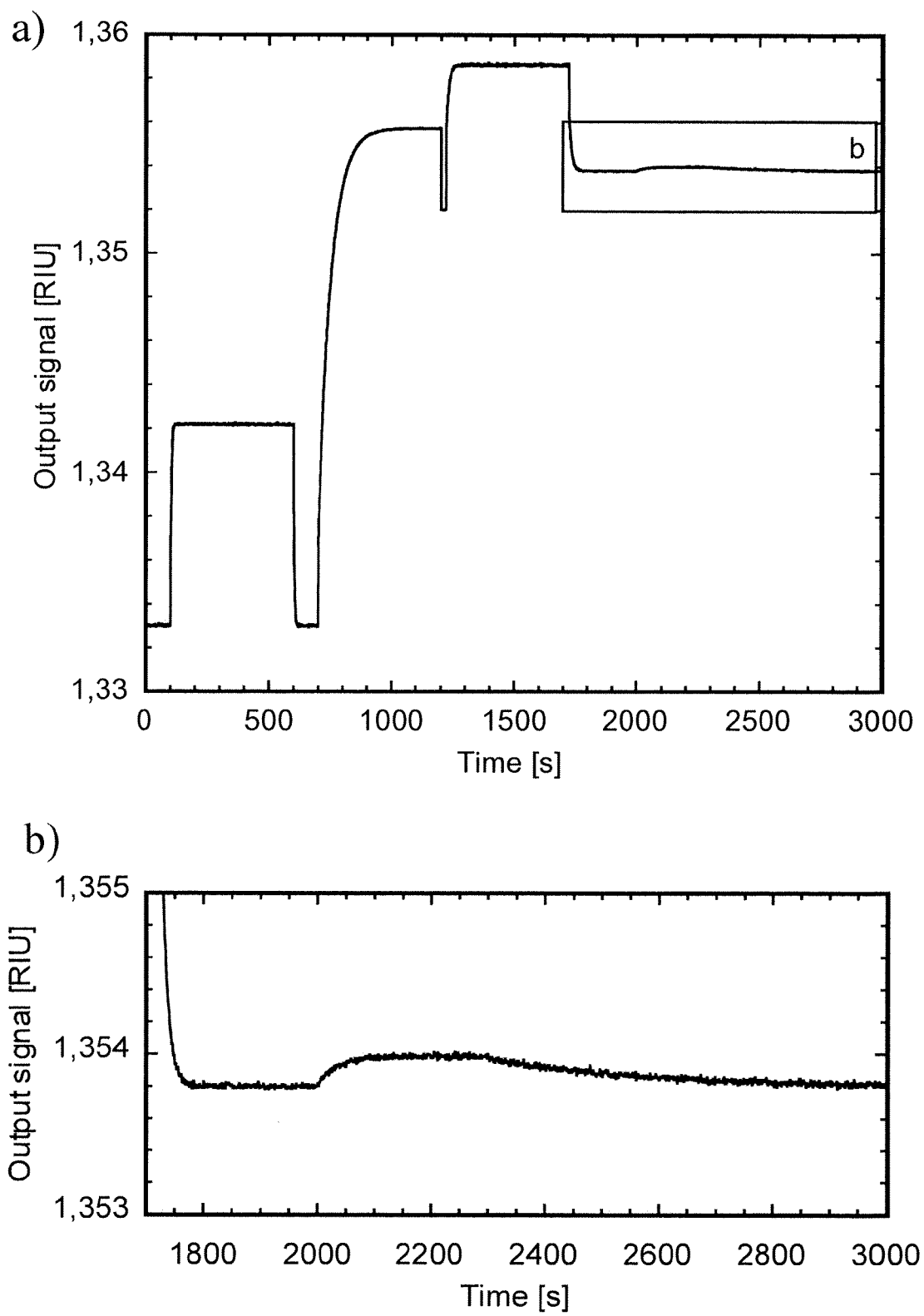

By repeatedly calculate the output signal in color/hue value or calibrated effective refractive index (or other parameter, such as surface concentration or film thickness) a vector of values are created, that can be used to monitor physical, chemical and biochemical reactions, as shown in FIGS. 17*a* and *b*. Concentration of substances can be calculated, as well as affinity and reaction rate constants. Moreover, epitope mapping and allosteric interactions between molecules can be evaluated.

The invention claimed is:

1. A method for an apparatus with a radiation source 100 which has means for irradiation 610 of electromagnetic radiation with a plurality of wavelengths onto a sensor surface 210 which supports a surface plasmon, and said radiation is reflected onto at least one photosensitive detector 300, and create reflectance values, characterized by that said wavelengths at said detector are separated by wavelength, forming a wavelength ensemble, in such way that a continuous response signal can be calculated using at least three of said wavelength reflectance values, finding the wavelength closest to the resonance condition and use of adjacent wavelengths to calculate said continuous response signal 510 being a function of an effective refractive index at said sensor surface 210, where, if the resonance wavelength is the first or last of said wavelengths, at least two adjacent wavelengths closest to said closest wavelength to said resonance condition are used to calculate said continuous response signal.

2. The method according to claim 1, whereas said sensor surface is irradiated by discrete wavelengths.

3. The method according to claim 2, whereas said plurality of wavelengths are less than 10.

4. The method according to claim 1, whereas said plurality of wavelengths are more than 3 and less than 10.

5. The method according to claim 1, whereas a set of three wavelengths are chosen in said ensemble-of wavelengths, and it is possible to change the properties of said apparatus by changing wavelength set.

6. The method according to claim 5, whereas change of said properties includes one or more of following properties: change of dynamic range, change of linearity, change of signal to noise ratio.

7. The method according to claim 6, whereas said wavelengths are narrow bands, less than 50 nm.

8. The method according to claim 7, whereas said reflectance values are used to calculate a response signal using at least one of the method, Oligo-Lambda, polynomial curve fitting, centroid or weighted centroid.

9. The method according to claim 8, whereas the closest wavelength to the resonance condition, and the two adjacent wavelengths are used to calculate said response signal, except when the first and last wavelength is closest to the resonance condition, for which the two wavelengths closest to the wavelength closest to the resonance condition are used to calculate said response signal and said wavelengths are narrow bands between 5 nm and 25 nm.

10. The method according to claim 1, whereas said response signal is calculated by a quotient, where the numerator is the difference in reflectance values between the two wavelengths closest to the wavelength at the resonance condition, and where there is an opposite sign depending on if the reflectance value of the adjacent wavelength to the wavelength closest to the resonance condition is from a lower or higher wavelength compared to the wavelength closest to the resonance condition, and where the denominator is the difference in reflectance between the wavelength closest to the resonance condition and the adjacent wavelength that has a reflectance level that is most far from the reflectance level of the wavelength that is closest to the resonance condition, and that a number, is added to said quotient, to secure that the response signal is continuous when wavelength set is changed.

11. The method according to claim 1, whereas said wavelengths are chosen such as, when said effective refractive index at said sensor surface has a value such as the two wavelengths that are closest to the resonance condition have the same reflectance level, and that the adjacent wavelengths to these said two wavelengths, have the same, or close to the same level, too.

12. The method according to claim 1, whereas said response signals are calibrated or normalized, creating an output signal.

13. The method according to claim 12, whereas said calibration and normalization are fulfilled by discrete calibration points to form a calibration curve, which are placed at least one in each segment defined by the wavelength closest to the resonance condition.

14. The method according to claim 13, whereas said calibration curve is a cubic spline.

15. The method according to claim 14, whereas said calibration curve is divided into segments, which overlaps response signal segments defined by which wavelength is closest to said resonance condition.

16. The method according to claim 15, whereas said calibration curves have at least one pseudo calibration point inserted at or close to the border between said response signal segments.

17. The method according to claim 16, whereas said overlapping calibration curves at said response signal segment borders, are weighted and summed.

18. The method according claim 12, whereas said output signal is collected in a time series.

19. The method according to claim 1, whereas said reflectance values are extrapolated, which gives the opportunity to obtain a larger dynamic range.

20. An apparatus with a radiation source 100 which has means for irradiation 610 of electromagnetic radiation with a plurality of wavelengths onto a sensor surface 210 which can support a surface plasmon, and said radiation is reflected onto at least one photosensitive detector 300, and create reflectance values, characterized by that said wavelengths at said detector are separated by wavelength, forming a wavelength ensemble, in such way that a continuous response signal can be calculated using at least three of said wavelength reflectance values, an arithmetic unit for finding the wavelength closest to the resonance condition and use of adjacent wavelengths to calculate said continuous response signal 510 being a function of an effective refractive index at said sensor surface 210, where, if the resonance wavelength is the first or last of said wavelengths, at least two adjacent wavelengths closest to said closest wavelength to said resonance condition are used to calculate said continuous response signal.

21. The apparatus according to claim 20, whereas said sensor surface is 2-dimensional and said photosensitive detector is 2-dimensional.

\* \* \* \* \*